(12) United States Patent
Sikora et al.

(10) Patent No.: US 11,925,363 B2
(45) Date of Patent: Mar. 12, 2024

(54) SYSTEM AND METHOD FOR JOINT RESURFACING AND REPAIR

(71) Applicant: ARTHROSURFACE INCORPORATED, Franklin, MA (US)

(72) Inventors: George Sikora, Bridgewater, MA (US); Steven W. Ek, Bolton, MA (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 78 days.

(21) Appl. No.: 17/543,420

(22) Filed: Dec. 6, 2021

(65) Prior Publication Data

US 2022/0338884 A1 Oct. 27, 2022

Related U.S. Application Data

(63) Continuation of application No. 16/430,947, filed on Jun. 4, 2019, now Pat. No. 11,191,552, which is a
(Continued)

(51) Int. Cl.

| | |
|---|---|
| A61B 17/17 | (2006.01) |
| A61B 17/16 | (2006.01) |
| A61F 2/28 | (2006.01) |
| A61F 2/30 | (2006.01) |
| A61F 2/38 | (2006.01) |

(52) U.S. Cl.
CPC .......... *A61B 17/17* (2013.01); *A61B 17/1637* (2013.01); *A61B 17/1675* (2013.01); *A61B 17/1739* (2013.01); *A61B 17/1764* (2013.01); *A61F 2/28* (2013.01); *A61F 2/30756* (2013.01); *A61F 2/3859* (2013.01); *A61B 17/16* (2013.01); *A61F 2002/30232* (2013.01); *A61F 2002/30617* (2013.01); *A61F 2002/3082* (2013.01); *A61F 2002/30878* (2013.01); *A61F 2002/30884* (2013.01); *A61F 2002/3895* (2013.01); *A61F 2310/00179* (2013.01); *A61F 2310/00982* (2013.01)

(58) Field of Classification Search
CPC ........................... A61B 17/17; A61B 17/1637
See application file for complete search history.

(56) References Cited

U.S. PATENT DOCUMENTS

| 2,919,692 A | * | 1/1960 | Ackermann | ....... A61B 17/1671 |
| | | | | 606/184 |
| 5,411,504 A | * | 5/1995 | Vilas | ...................... A61B 17/17 |
| | | | | 606/87 |

(Continued)

*Primary Examiner* — Christian A Sevilla
(74) *Attorney, Agent, or Firm* — Goodwin Procter LLP

(57) ABSTRACT

An implant resection system for preparing an implant site to replace a defect in an articular surface of a first bone includes a first guide configured to be coupled generally to the first bone. The first guide includes a body portion defining a channel configured to receive a pin, wherein the pin is configured to penetrate and form a longitudinally disposed bore within the first bone. The implant resection system further includes a second guide configured to be coupled generally perpendicular to the first bone proximate to the defect by way of the bore. The second guide includes a drill bit configured to form an excision site through a portion of the articular surface in preparation of receipt of an implant.

20 Claims, 19 Drawing Sheets

Related U.S. Application Data continuation of application No. 15/296,772, filed on Oct. 18, 2016, now Pat. No. 10,307,172, which is a continuation of application No. 13/930,737, filed on Jun. 28, 2013, now Pat. No. 9,468,448.

(60) Provisional application No. 61/667,562, filed on Jul. 3, 2012.

(56) References Cited

U.S. PATENT DOCUMENTS

| | | | | |
|---|---|---|---|---|
| 5,964,805 | A * | 10/1999 | Stone | A61F 2/4618 424/423 |
| 7,618,451 | B2 * | 11/2009 | Berez | A61B 34/20 606/88 |
| 7,815,681 | B2 * | 10/2010 | Ferguson | A61B 17/7059 606/71 |
| 9,468,448 | B2 * | 10/2016 | Sikora | A61B 17/17 |
| 2003/0130741 | A1 * | 7/2003 | McMinn | A61B 17/1668 606/89 |
| 2004/0082906 | A1 * | 4/2004 | Tallarida | A61B 17/0684 604/43 |
| 2004/0230315 | A1 * | 11/2004 | Ek | A61B 17/1764 623/901 |
| 2004/0254585 | A1 * | 12/2004 | Whittaker | A61B 17/1714 606/104 |
| 2005/0090905 | A1 * | 4/2005 | Hawkins | A61L 27/34 623/23.51 |
| 2008/0015607 | A1 * | 1/2008 | D'Alessio | A61F 2/4684 606/87 |
| 2008/0177200 | A1 * | 7/2008 | Ikehara | A61B 10/025 600/567 |
| 2009/0228031 | A1 * | 9/2009 | Ritter | A61B 17/1635 606/167 |
| 2009/0254094 | A1 * | 10/2009 | Knapp | A61B 17/1637 606/104 |
| 2010/0217315 | A1 * | 8/2010 | Jolly | A61B 17/06 606/223 |
| 2010/0249935 | A1 * | 9/2010 | Slivka | A61F 2/4684 623/17.11 |
| 2012/0065734 | A1 * | 3/2012 | Barrett | A61F 2/4455 623/17.16 |
| 2013/0237987 | A1 * | 9/2013 | Graham | A61B 17/151 606/87 |
| 2015/0265328 | A1 * | 9/2015 | Viola | A61B 17/1615 606/104 |
| 2016/0022374 | A1 * | 1/2016 | Haider | A61B 17/142 606/96 |
| 2018/0154041 | A1 * | 6/2018 | Altschuler | A61F 2/30756 |

* cited by examiner

SYSTEM AND METHOD FOR JOINT RESURFACING AND REPAIR

CROSS-REFERENCE TO RELATED APPLICATIONS

This application is a continuation of U.S. patent application Ser. No. 16/430,947 (now U.S. Pat. No. 11,191,552), filed Jun. 4, 2019, which is a continuation of U.S. patent application Ser. No. 15/296,772, (now U.S. Pat. No. 10,307,172), filed Oct. 18, 2016, which is a continuation of U.S. patent application Ser. No. 13/930,737 (now U.S. Pat. No. 9,468,448), filed Jun. 28, 2013, which claims the benefit of U.S. Provisional Patent Application Ser. No. 61/667,562, filed Jul. 3, 2012, the contents of which are fully incorporated herein by reference.

FIELD

This disclosure relates to the repair of defects that occur on the surface of bones, and, more particularly, devices and methods for the repair of defects that occur in articular cartilage on the surface of bones of the tibiofemoral joint, or knee joint.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

Figure 1:
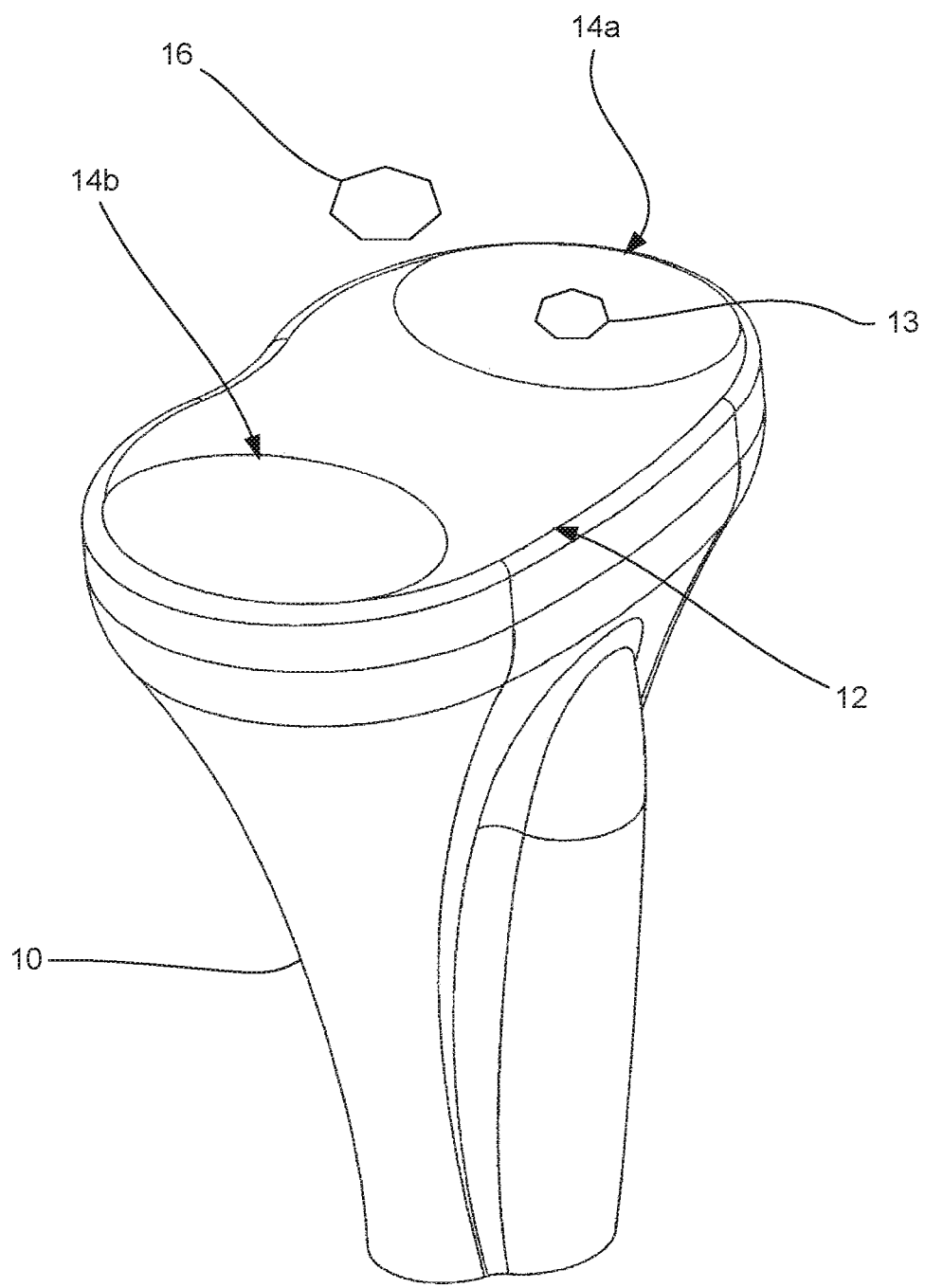
FIG. 1 is a schematic diagram illustrating an incision proximate the knee.

By way of summary, one embodiment of the present disclosure may feature a system and method for repairing a portion of the articular surface proximate to a defect. While the present disclosure will be described in terms of a system and method for repairing a portion of the tibial and femoral articular surfaces, it should be understood that the system and method may be used to repair other articular surfaces (such as, but not limited to, humeral articular surfaces and the like).

The system and method may include securing a guide defining one or more passageways to a portion of the tibia (e.g., immediately below the tibial articular surface) proximate to the defect. The passageways may define a generally cylindrical core pathway for one or more alignment pins to pass through. When the alignment pins are secured to the tibia, a first truncated cylindrical excision site may be formed in the articular surface and/or bone beneath the articular surface by advancing a drill bit (i.e., a coring drill bit) along the alignment pins. The drill may have a diameter large enough to remove a portion of the articular surface as it is advanced through the guide and into the articular surface. Additional truncated cylindrical excision sites may also be formed. One or more of the additional truncated cylindrical excision sites may partially overlap with adjacent truncated cylindrical excision sites.

The guide and/or the drill may include a depth feature configured to control the depth of the truncated cylindrical excision site formed in the articular surface/bone of the tibia. The depth feature may prevent the drill from being advanced too far, thereby preventing the drill from accidentally damaging any structures proximate to the excision sites (e.g., nerves). The system and method may also include a tibial implant having a load bearing surface having a surface contour/geometry based on the surface contour/geometry of the patient's original removed articular surface of the tibia. For example, the surface contour/geometry of the load bearing surface may be based on one or more measurements taken of the patient's original articular surface. The implant may also feature a bone facing or distal surface having a surface contour/geometry configured to be received in the truncated cylindrical excision sites.

The system and method may further include a first guide for aligning and securing a second drill guide to a portion of the femur (e.g., lateral or medial femoral condyle) proximate to the defect. The first guide may define a channel for receiving and retaining a pin. Upon advancing the pin through the channel of the first guide in a direction towards the femur, the pin may engage and pierce the bone to form a bore within a portion of the femur (e.g., femoral condyle). The system and method may further include securing the second drill guide defining one or more passageways to a portion of the femur (e.g. femoral condyle). At least one of the passageways may define a generally cylindrical core pathway for a support rod to pass therethrough and secure the second drill guide to the femur. Another passageway may define a generally cylindrical core pathway for a drill bit (i.e., a router drill bit). The support rod may serve as an axis about which the drill bit may rotate. An excision site may be formed in the articular surface of a femoral condyle and/or bone beneath the articular surface by rotating the drill guide, and the drill bit, about the support rod. The drill may have a diameter large enough to remove a portion of the articular surface as it is rotated about the support rod and into the articular surface.

The second drill guide and/or the drill may include a depth feature configured to control the depth of the excision site formed in the articular surface/bone of the femoral condyle of the femur. The depth feature may prevent the drill from being advanced too far, thereby preventing the drill from accidentally damaging any structures proximate to the excision site (e.g., nerves). The system and method may also include a femoral condyle implant having a load bearing surface having a surface contour/geometry based on the surface contour/geometry of the patient's original removed articular surface of the femur. For example, the surface contour/geometry of the load bearing surface may be based on one or more measurements taken of the patient's original articular surface. The implant may also feature a bone facing or distal surface having a surface contour/geometry configured to be received in the excision site.

Turning now to FIG. 1, a tibia 10 is generally illustrated. As may be appreciated, the tibial articular surface 12 may include a tibial plateau comprising a plurality of concaved surfaces 14a, 14b configured to articulate with the femoral condyles (not shown for clarity). It may be further appreciated that the tibial articular surface 12 may include additional concaved surfaces not shown for the sake of clarity. One or more of the concaved surfaces (e.g., concaved surface 14a) may include a defect 13 in the tibial articular surface 12 to be repaired. On the distal side of the tibia 10, a nerve bundle 16 is located. As described herein, the system and method according to one embodiment of the present disclosure may be configured to avoid damaging the nerve bundle when forming the excision site(s).

For illustrative purposes, the following will describe a system and method for preparing an implant site on the tibial articular surface including two partially overlapping truncated cylindrical excision sites and an implant configured to fit therein. As may be appreciated, the system and method according to the present disclosure may be used to form an implant site having greater than or fewer than two partially overlapping truncated cylindrical excision sites. As will be evident from the following description, the truncated cylindrical excision sites may be formed by drilling along the anterior-posterior plane (i.e., from an anterior face of the tibia 10 and extending generally towards the posterior face of the tibia 10).

Figure 2:
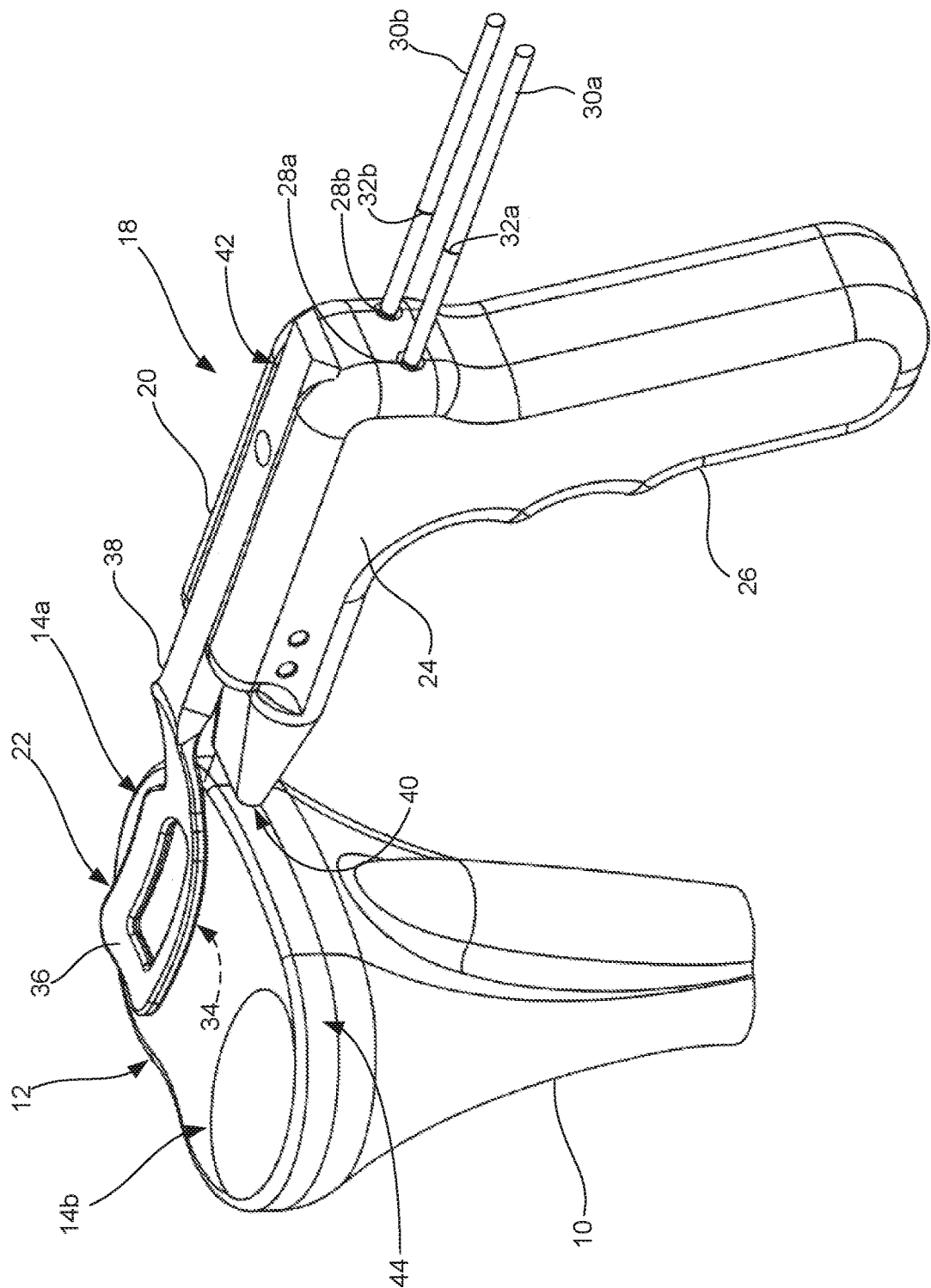
FIG. 2 is a perspective view illustrating one embodiment of a guide coupled to the tibia consistent with the present disclosure.
Figure 3:
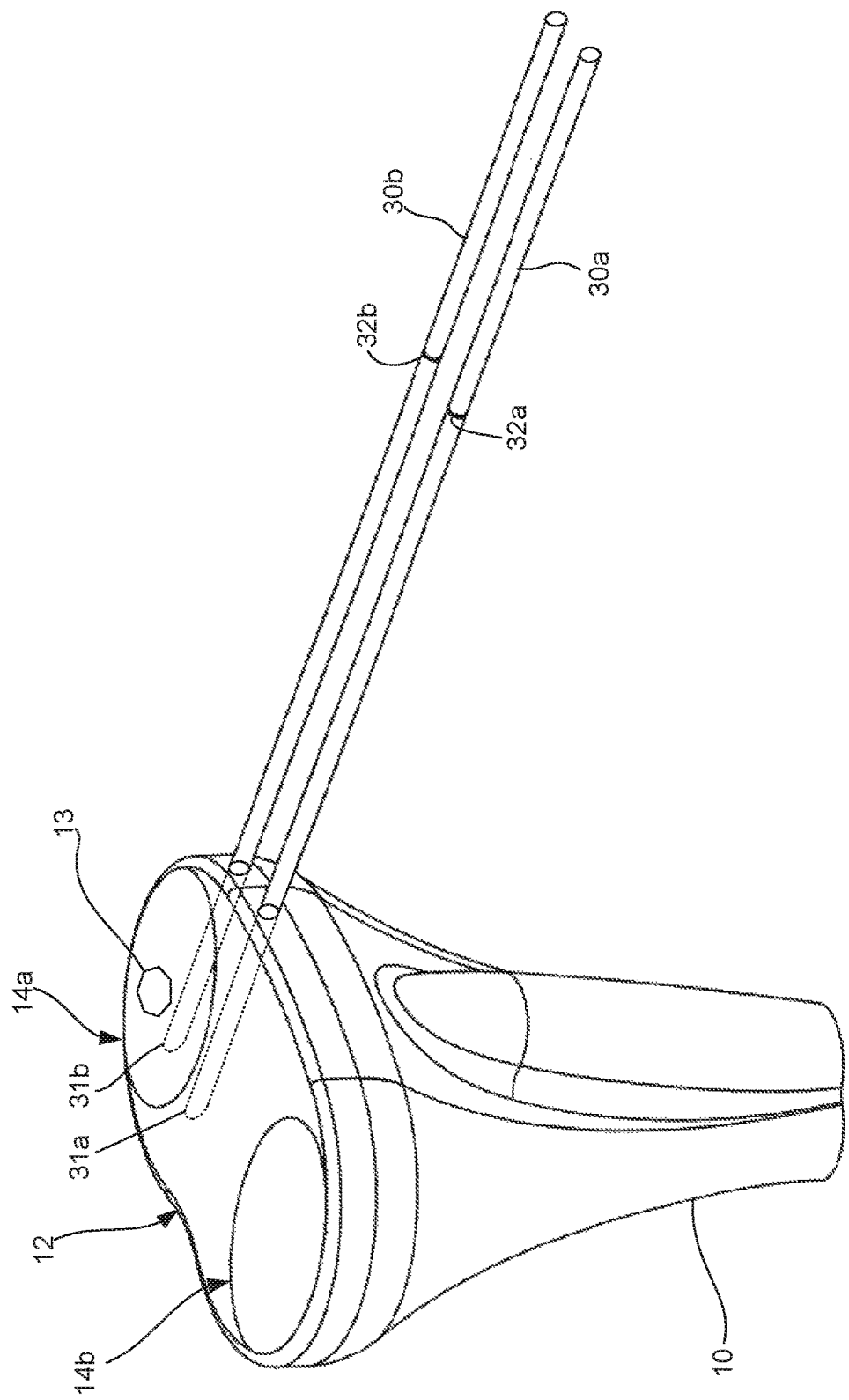
FIG. 3 is a perspective view illustrating pins advanced within the guide and into the tibia consistent with the present disclosure.

Turning now to FIG. 2, one embodiment of a guide 18 secured to the tibia 10 is generally illustrated consistent with the present disclosure. The guide 18 may include a jig 20 and a spoon 22. The jig 20 may include a body portion 24 and a handle portion 26 extending therefrom. The body portion 24 may define at least two passageways 28a, 28b. The passageways 28a, 28b may each define a generally cylindrical pathway for alignment pins 30a, 30b. The alignment pins 30a, 30b may be advanced through the passageways 28a, 28b into the tibia 10, as generally illustrated in FIG. 3. The alignment pins 30a, 30b may include a depth feature 32a, 32b configured to control the depth of the pins 30a, 30b in the bone 10 (i.e., to prevent the pins 30a, 30b from being set too deep or too shallow into the bone 10). The depth feature 32a, 32b may comprise an indicia (e.g., but not limited to, a laser marking, groove, or the like) which may be aligned with the proximal end of the passageways 28a, 28b. The alignment pins 30a, 30b may be configured to generally align a drill bit with a desired are of bone 10 to be cut and to maintain alignment of the drill bit during excision of the bone 10, as described in greater detail herein.

The position of the jig 20 (and in particular, the passageways 28a, 28b) may be set based on, at least in part, the spoon 22. In particular, the spoon 22 may include a generally convex base portion 34 having a surface contour substantially corresponding to the curvature of the concaved surface 14a being repaired (e.g., the concaved surface 14a which has the defect 13). An upper portion 36 of the spoon 22 may have a generally concaved surface (e.g., generally corresponding to the curvature of the concaved surface 14a being repaired). The spoon 22 may have a cross-sectional thickness configured to facilitate advancement of the spoon 22 between the tibial articular surface 12 and the femoral condyles (shown in FIG. 9, for example). For example, the cross-sectional thickness of the spoon 22 may be selected to provide sufficient rigidity to align the jig 20 relative to the tibial articular surface 12 (and in particular, the defect 13 on the concaved surface 14a) while also minimizing the required separation between the tibia 10 and the femur.

The spoon 22 may be an integral component of the jig 20 (e.g., a unitary or single one-piece structure) or may be configured to be releasably coupled to the jig 20. For example, in the illustrated embodiment, the spoon 22 may include an arm portion 38 configured to extend generally outwardly from a distal face 40 (e.g., a bone facing surface) of the jig 20. As shown, the body 24 of the jig 20 may include a channel 42 shaped and/or sized to receive and retain a portion of the arm 38. The size and shape of the arm portion 38 may be configured to allow a portion of the distal face 40 to be disposed proximate to the perimeter (e.g., proximate to the meniscus 44) when the spoon 22 is disposed on the concaved surface 14a such that the first and second passageways 28a, 28b partially overlap with the tibial articular surface 12.

In practice, the guide 18 may be positioned relative to the defect 13 on the concaved surface 14a by advancing the spoon 22 between the tibial articular surface 12 and the femur such that the base portion 34 of the spoon 22 is disposed over at least a portion of the defect 13 on the tibial articular surface 12. The spoon 22 may be advanced until the distal face 40 of the jig 20 generally abuts against a portion of the tibia 10 (e.g., proximate to the meniscus 44). The size and shape of the base portion 34 as well as the arm portion 38/distal face 40 may be configured to generally center the spoon 22 within the concaved surface 14a. Once the spoon 22 is positioned over the defect 13, the alignment pins 30a, 30b may be advanced through the passageways 28a, 28b and into the tibia 10, as shown in FIG. 3. It should be noted that internal features and/or surfaces are illustrated in phantom in FIG. 3. As shown, distal ends 31a, 31b of the alignment pins 30a, 30b may engage and pierce the bone 10, thereby securely coupling the alignment pins 30a, 30b to the bone 10.

Figure 4:
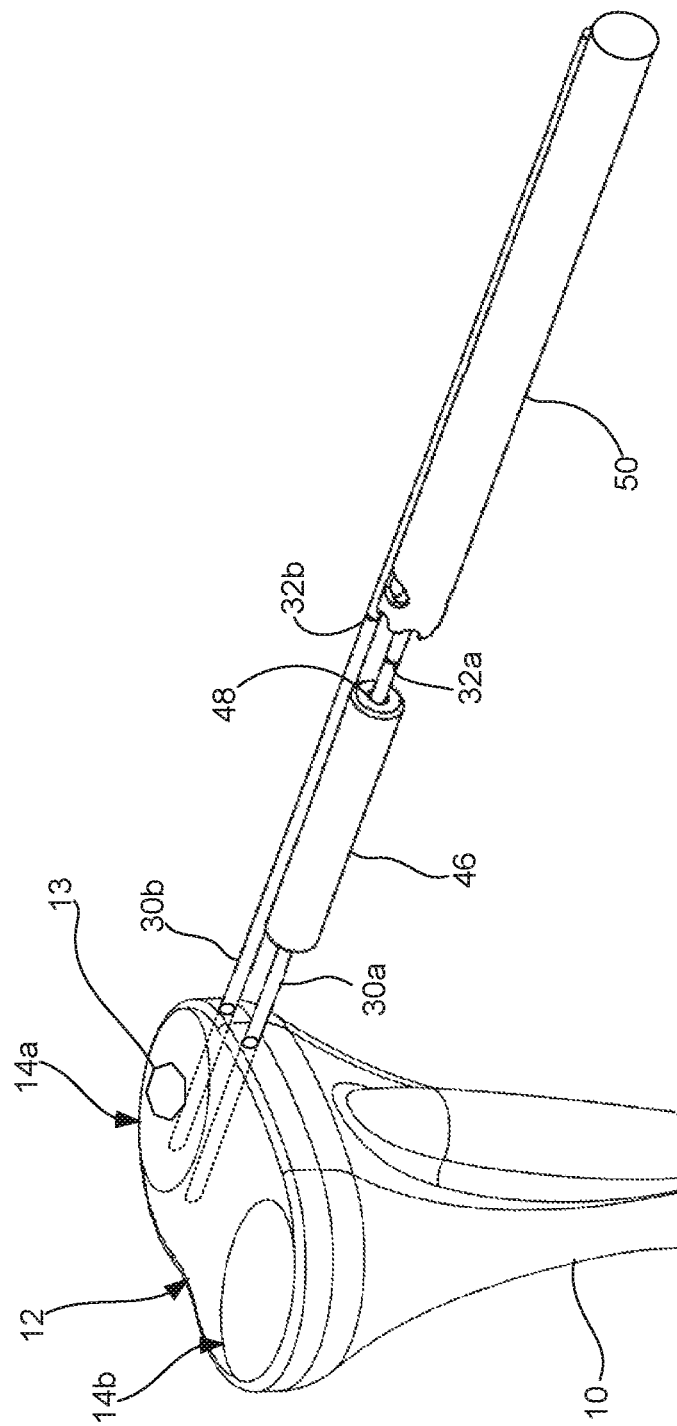
FIG. 4 is a perspective view illustrating a drill bit advanced onto one of the pins consistent with the present disclosure.

Turning now to FIG. 4, upon advancing the alignment pins 30a, 30b into the bone 10, the guide 18 may be removed from the bone 10. As such, the alignment pins 30a, 30b may remain within the bone 10 and may be configured to provide alignment of a drill bit with the bone 10 to form first and second excision sites. In the illustrated embodiment, a bushing 46 may be advanced along the alignment pins 30a, 30b and against the bone 10. For example, the bushing 46 may include a longitudinally disposed passageway 48 shaped and/or sized to receive at least the first alignment pin 28a. The bushing 46 may be advanced along the alignment pin 28a until the bushing 46 engages against (e.g., abuts) a portion of the tibia 10 (e.g., proximate to the meniscus 44). A cannulated drill 50 may then be advanced over the bushing 46 and the alignment pin 28a and into the bone 10 to form a first truncated cylindrical excision site (shown in FIG. 6). Upon forming the first excision site, the drill 50 and bushing 46 may be removed from the first alignment pin 28a and then placed over and advanced along the second alignment pin 28b to form a second truncated cylindrical excision site in the bone 10 (shown in FIG. 6).

Figure 5:
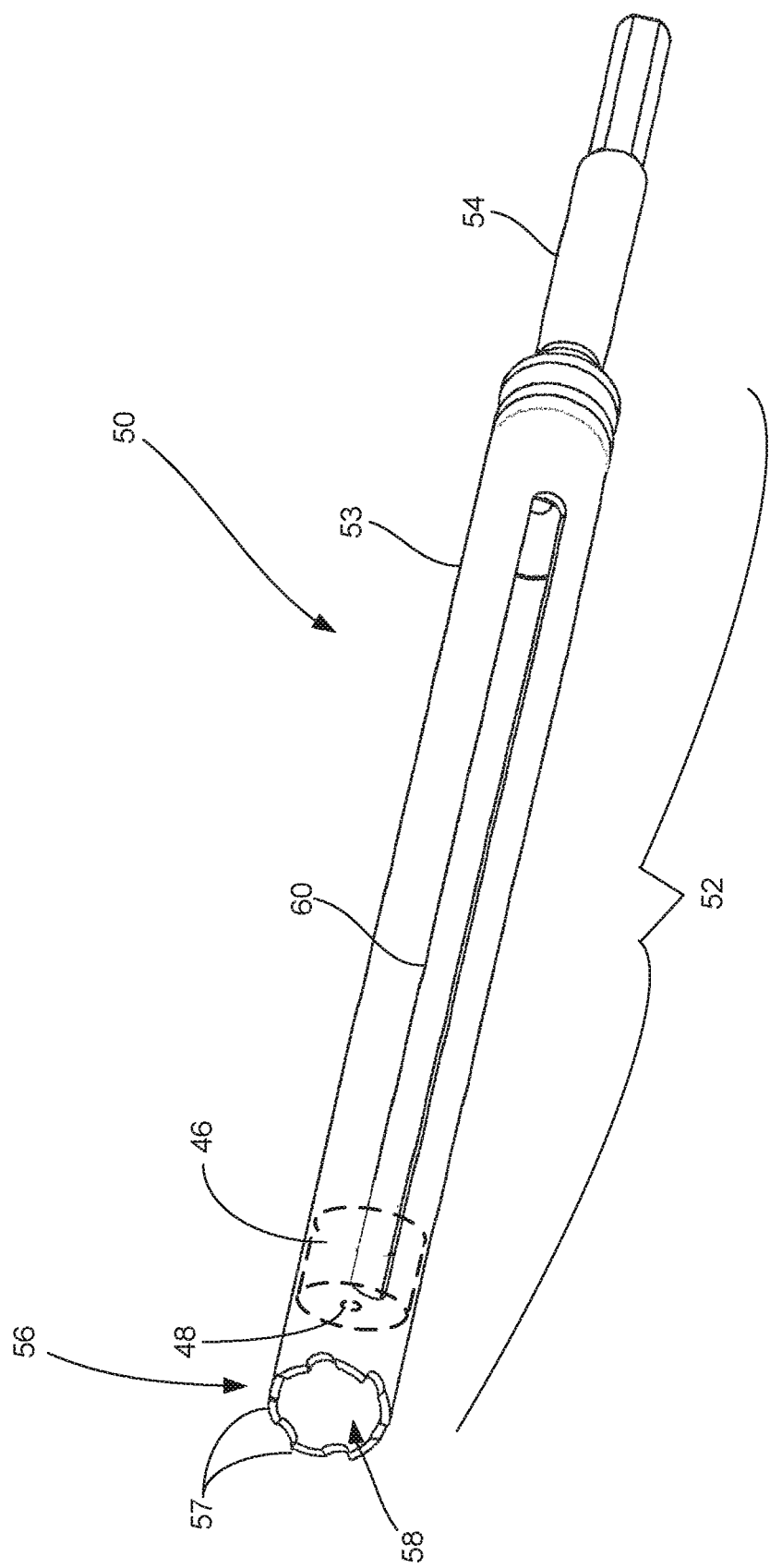
FIG. 5 is a perspective view of one embodiment of a drill bit consistent with the present disclosure.

One embodiment of a cannulated drill 50 is generally illustrated in FIG. 5. The cannulated drill 50 may feature a core drill bit 52 having a barrel portion 53 and optionally a shank portion 54 extending from the barrel portion 53. The shank portion 54 may include a multi-faceted proximal end configured to be secured to a drill (e.g., a hand drill, electric drill, pneumatic drill or the like). Alternatively, a proximal end of the core drill bit 52 may be directly coupled to the drill.

The core drill bit 52 may include a cutting surface 56 (for example, comprising a plurality of cutting teeth 57) disposed about a distal end of the barrel portion 53. The cutting surface 56 may be evenly disposed around the generally circular distal end of the barrel portion 53. The barrel portion 53 may define a core cavity 58 configured to receive the removed portion of the tibial articular surface 12 and bone 10. As may be appreciated, the only portion of the tibial articular surface 12 and bone 10 that is cut by the core drill bit 50 corresponds to the thickness of the cutting surface 56, which itself is a function of the wall thickness of the barrel 53. As such, these thicknesses may be selected to remove the least amount of material while also providing the necessary rigidity and/or strength to the core drill bit 50.

The core drill bit 52 may optionally feature one or more windows 60 disposed along the length of the barrel portion 53. The window 60 may allow air, fluid, and cutting chips to exit the barrel portion 53. In addition, the window 60 may also allow the user to align the core drill bit 52 with the alignment pins 30a, 30b to control the depth of the excision site (i.e., the length of the excision site as measured across the tibial articular surface 12).

As shown, the core drill bit 52, particularly the barrel portion 53, may be shaped and/or sized to receive the bushing 46 configured facilitate alignment of the core drill bit 52 as the core drill bit 52 is advanced into the tibial articular surface 12 and bone 10. The bushing 46 may be translatably disposed along the longitudinal axis of the core drill bit 52 and may include a passageway 48 configured to receive the alignment pins 30a, 30b. For example, the bushing 46 may be initially located near the distal end of the barrel portion 53. As the core drill bit 52 is advanced towards the bone 10, an alignment pin 30a, 30b may be received in the passageway 48 and the bushing 46 may translate towards the proximal end.

As the drill bit 50 is advanced towards the bone 10, a portion of the cutting surface 56 may engage the tibial articular surface 12 and/or the bone 10, thereby forming a truncated cylindrical excision site. Once the drill bit 50 has been advanced to create the first excision site, the second truncated cylindrical excision site may be formed. For example, the bushing 46 and drill bit 50 may be removed from the first alignment pin 30a and placed on the second alignment pin 30b and the drill bit 50 may be advanced toward the bone 10 in a manner similar to that described herein. Although the same bushing 46 and drill bit 50 are described as being used to create the first and second excision sites, a second bushing and drill bit may be used with the second alignment pin 30b to create the second excision site, wherein the first and second drill bits may have the same or different outer diameters.

Figure 6:
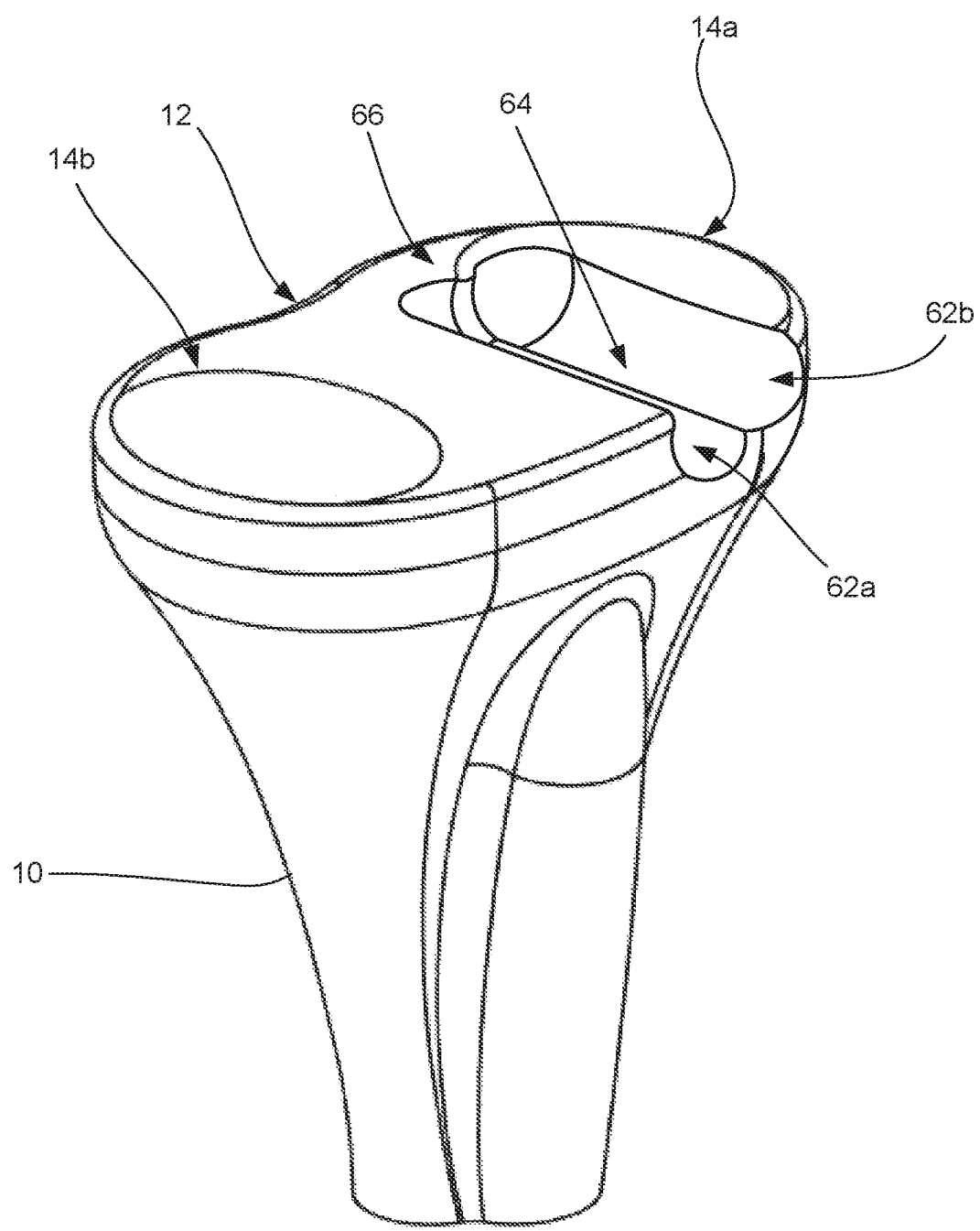
FIG. 6 illustrates one embodiment of a first and second excision site formed on the tibial articular surface using the drill bit consistent with the present disclosure.

FIG. 6 generally illustrates one embodiment of the first and the second truncated cylindrical excision sites 62a, 62b corresponding to the drill bit 50 and the first and second alignment pins 30a, 30b. Although shown as being truncated, in other embodiments, the first and second excision sites 62a, 62b may be separated by a distance generally perpendicular to the longitudinal axes of the first and second alignment pins 30a, 30 such that the first and the second truncated cylindrical excision sites 62a, 62b do not overlap.

The resulting implant site may therefore include the first and second truncated cylindrical excision sites 62a, 62b, wherein the first and second truncated cylindrical excision sites 62a, 62b partially overlap with one another. The truncated cylindrical excision sites 62a, 62b may be centered/revolved around the alignment pins 30a, 30b and may extend along the articular surface 12 generally along the anterior-posterior plane. For example, the truncated cylindrical excision sites 62a, 62b may extend from the anterior face of the tibial articular surface 12 generally towards the posterior face. The implant site may therefore include a base portion 64 including two overlapping truncated cylindrical extensions or scallops defined by the two excision sites 62a, 62b. The resulting implant site therefore may generally eliminate/reduce the occurrence of 90 degree cuts and therefore more evenly distribute loads/forces to the bone 10 compared a traditional 90 degree notch cut.

The truncated cylindrical excision sites 62a, 62b have been illustrated extending partially across the tibial articular surface 12 (i.e., one or more of the truncated cylindrical excision sites 62a, 62b do not extend completely across the articular surface 12 thus leaving a portion 66 of the tibial articular surface 12 and/or bone 10 remaining). This embodiment may be particularly beneficial since it further minimizes the potential for accidentally damaging the nerve bundle. However, the system and method according to the present disclosure may also allow for one or more of the truncated cylindrical excision sites 62a, 62b to extend completely across the articular surface 12.

Figure 7:
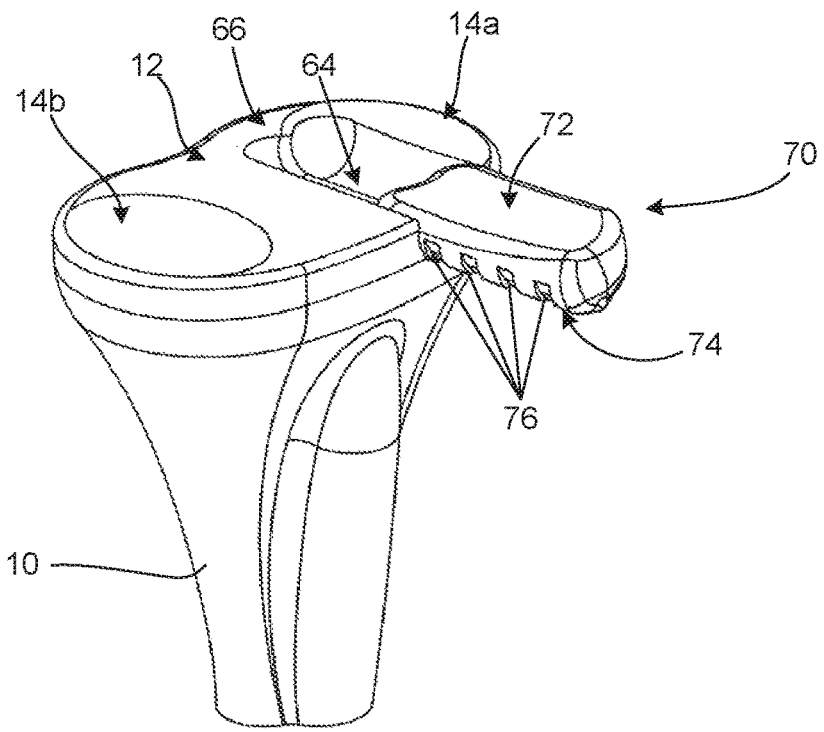
FIGS. 7 and 8 are perspective views illustrating one embodiment of a tibial implant coupled to the first and second excision site of the tibial articular surface consistent with the present disclosure.
Figure 8:
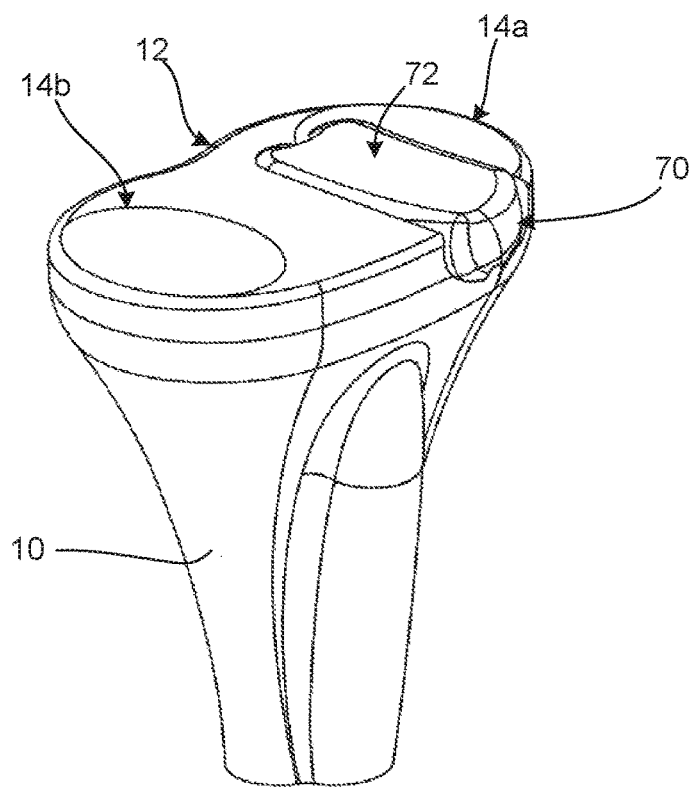

Turning now to FIGS. 7 and 8, one embodiment of an implant 70 coupled to the first and second excision sites of the tibia consistent with the present disclosure is generally illustrated. The implant 70 may include a load bearing surface 72 and a bone facing or distal surface 74. The load bearing surface 72 may have a surface contour/geometry substantially corresponding to the contour/geometry of the removed tibial articular surface 12 proximate the defect 13. The contour/geometry of the load bearing surface may be based on a plurality of measurement take of the patient's tibial articular surface 12.

The bone facing surface 74 may have an overall contour/geometry generally corresponding to the contour/geometry of the base portion 64 of the first and second truncated cylindrical excision sites 62a, 62b and the removed bone 10. Optionally, the bone facing surface 74 may include one or more relief cavities, pockets and/or cross-cuts 76 configured to enhance securing the implant 70 to the bone 10 within the truncated cylindrical excision sites 62a, 62b. The relief cavities 76 may be configured to allow bone regrowth around a portion of the implant 70 and/or promote cement adhesion. As shown, the implant 70 may include a generally unitary structure (i.e., the implant 70 may be a solid, single-piece component). In one embodiment, the implant 70 may be made from ultra-high molecular weight polyethylene (UHMWPE) material. Additionally (or alternatively), the implant 70 may be made from a material based on donor tissue and/or synthetic bone and cartilage construct. For example, the implant 70 may include a ceramic porous base layer that defining the bone facing surface 74 and a collagen material disposed on a top portion thereof and defining the load bearing surface 72.

In other embodiments, the implant 70 may include multiple portions configured to be coupled together. Additionally, the implant 70 may optionally comprise one or more keels, tails, protrusions or the like, that extend generally downwardly from the bone facing surface 74 and away from the load bearing surface 72. The keels, tails, or protrusions may be configured to engage a corresponding notch (not shown) formed in the base portion 64 of the truncated cylindrical excision sites 62a, 62b.

As may be appreciated from FIGS. 7 and 8, an implant consistent with at least one embodiment of the present disclosure may have a non-planar load bearing surface 72. While some known tibial implants have had a generally planar or flat load bearing surface, an implant consistent with at least one embodiment of the present disclosure may have a concaved geometry which may better approximate the geometry of the patient's removed tibial articular surface 12.

Figure 9:
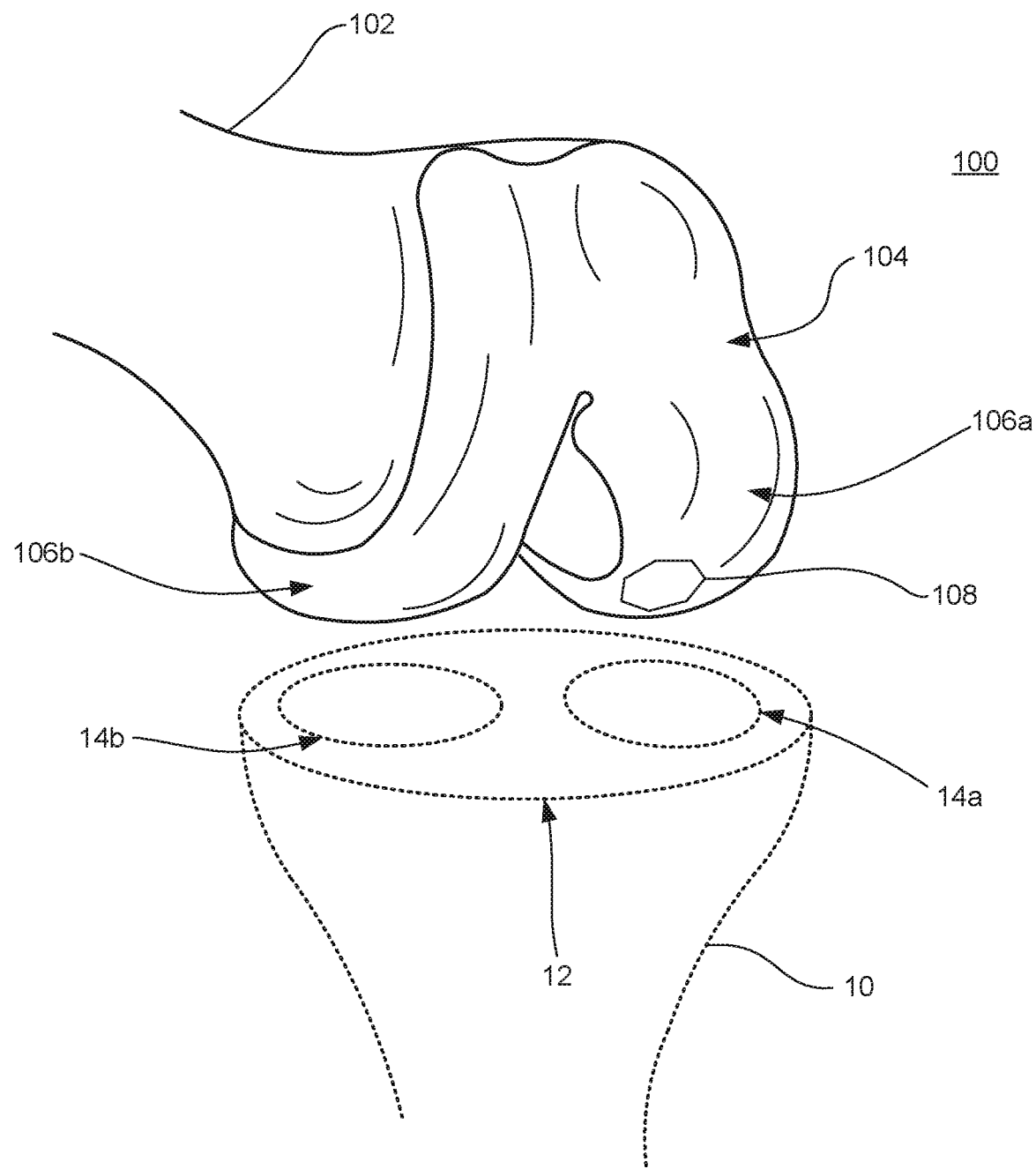
FIG. 9 is a schematic diagram illustrating an incision proximate the knee.

Turning now to FIG. 9, a knee joint 100 is generally illustrated. More specifically, the tibiofemoral components (i.e. tibia 10 and femur 102) are shown. The femur 102 may generally include femoral articular surface 104 that may include femoral condyles 106a, 106b configured to articulate with the tibial articular surface 12 and concaved surfaces 14a, 14b of the tibia 10. It may be further appreciated that the knee joint 100 include a patella (not shown for the sake of clarity). One of the femoral condyles (e.g., condyle 106) may include a defect 108 in the articular surface 104 to be repaired.

For illustrative purposes, the following will describe a system and method for preparing an implant site on the articular surface of a femoral condyle including an excision site and an implant configured to fit therein. As will be evident from the following description, the excision sites may be formed by drilling along the horizontal plane of a femoral condyle (i.e., from lateral to medial and/or vice versa).

Figure 10:
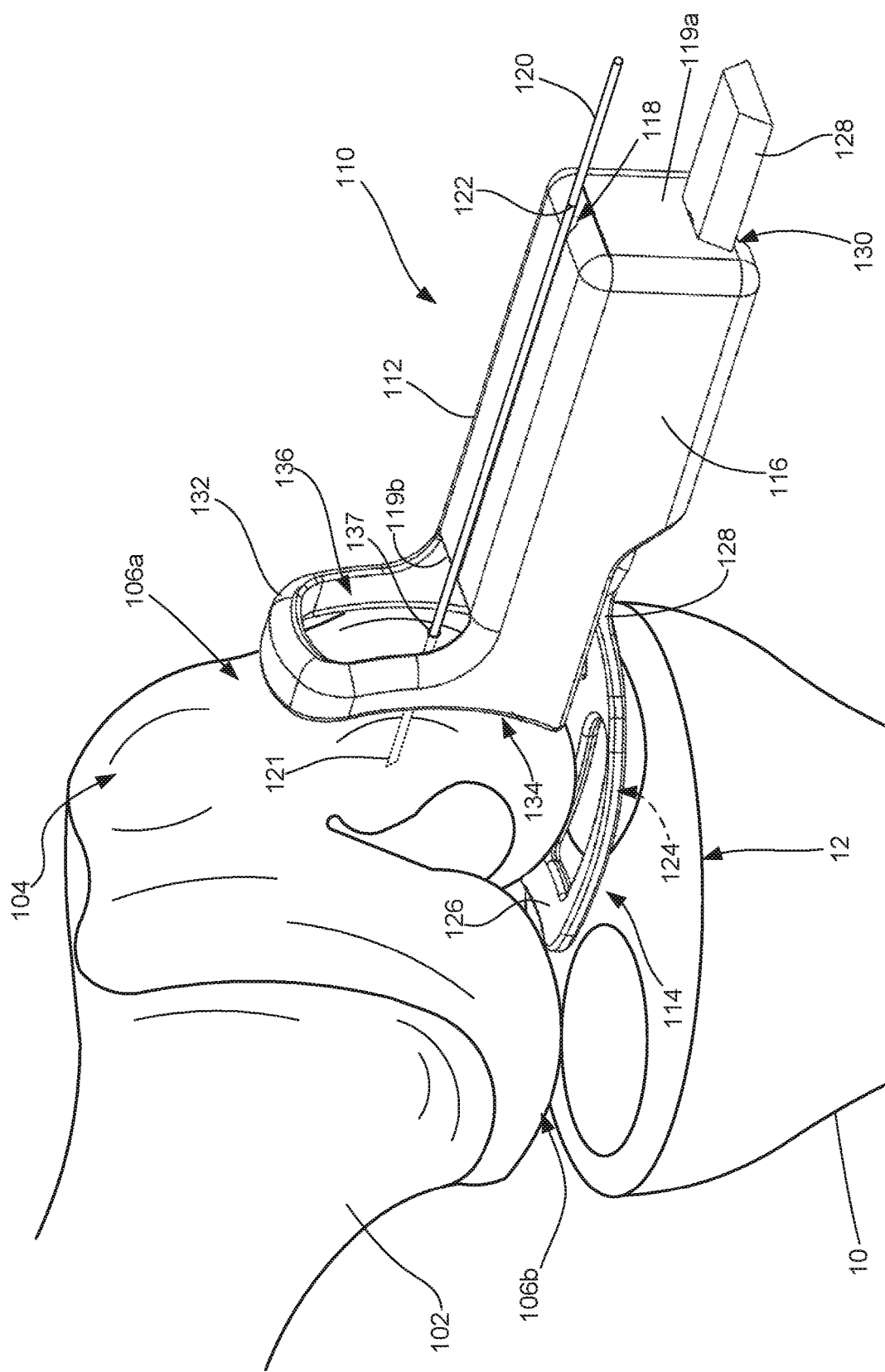
FIG. 10 is a perspective view illustrating one embodiment of a first guide coupled to the femur and having a pin advanced within the guide and into the femur consistent with the present disclosure.

Turning now to FIG. 10, one embodiment of a first guide 110 secured to a femoral condyle 106a of the femur 102 is generally illustrated consistent with the present disclosure. The first guide 110 may include a jig 112 and a spoon 114. The jig 112 may include a body portion 116 including at least one channel 118 longitudinally disposed on a portion thereof. The channel 118 may extend from a proximal end 119a to a distal end 119b of the body 116. The channel 118 may be shaped and/or sized to receive and retain a pin 120. As shown, the pin 120 may be advanced through the channel 118 and into the femur 102 (e.g. femoral condyle 106a). The pin 120 may further include a distal end 121 configured to engage and pierce the bone 102. The pin 120 may further include a depth feature 122 configured to control the depth of the pin 120 into the bone 102 (i.e., to prevent the pin 120 from being set too deep or too shallow into the bone 102). The depth feature 121 may include an indicia (e.g., but not limited to, a laser marking, groove, or the like) which may be aligned with the proximal end 119a of the body 116 of the first guide 110.

The position of the jig 112 (and in particular, the channel 118) may be set based on, at least in part, the spoon 114. As shown, the spoon 114 may include a generally convex base portion 124 having a surface contour substantially corresponding to the curvature of a concaved surface opposing the associated femoral condyle being repaired (e.g., the concaved surface 14a opposing the femoral condyle 106a which has the defect 108). An upper portion 126 of the spoon 114 may have a generally concaved surface (e.g., generally corresponding to the curvature of the femoral condyle 106a surface being repaired). The spoon 112 may have a cross-sectional thickness configured to facilitate advancement of the spoon 114 between the tibial articular surface 12 and the femoral condyles 106a, 106b. For example, the cross-sectional thickness of the spoon 112 may be selected to provide sufficient rigidity to align the jig 112 relative to the tibial articular surface 12 and one of the femoral condyles (and in particular, the defect 108 on the femoral condyle 106a) while also minimizing the required separation between the tibia 10 and the femur 102.

The spoon 112 may be an integral component of the jig 112 (e.g., a unitary or single one-piece structure) or may be configured to be releasably coupled to the jig 112. For example, in the illustrated embodiment, the spoon 114 may include an arm portion 128 configured to extend generally outwardly from the distal end 119b of the body 116 of the jig 112. As shown, the body 116 of the jig 112 may include a channel 130 shaped and/or sized to receive and retain a portion of the arm 128. In the illustrated embodiment, the jig 112 may further include an alignment member 132 extending from the distal end 119b of the body 116. The alignment member 132 may include a distal face 134 (e.g., a bone facing surface). The distal face 134 may have a generally concaved surface (e.g., generally corresponding to the curvature of the femoral condyle 106a surface being repaired).

The size and shape of the arm portion 128 may allow a portion of the distal face 134 of the alignment member 132 to be disposed proximate to the femoral condyle 106a when the spoon 114 is disposed between the tibial articular surface 12 and the femoral condyle 106a (and in particular, on the concaved surface 14a and the femoral condyle 106a) such that the channel 118 is aligned with a portion of the articular surface of the femoral condyle 106a. The alignment member 132 may further include a passageway 136. The passageway 136 may be shaped and/or sized to allow the pin 120 to pass through upon advancement towards the bone 102. The passageway 136 may further provide a user with visual observation of the penetration site 137 of the pin 120 into the bone 102.

In practice, the first guide 110 may be positioned relative to the defect 108 on articular surface of the femoral condyle 106a by advancing the spoon 114 between the tibial articular surface 12 and the femoral condyle 106a such that the upper portion 126 of the spoon 114 and/or distal face 134 of the alignment member 132 is disposed over at least a portion of the defect 108 on the articular surface of the femoral condyle 106a. The spoon 114 may be advanced until the distal face 134 of the alignment member 132 generally abuts against a portion of the femoral condyle 106a. The size and shape of the base portion 124 and upper portion 126 of the spoon 112, as well as the arm portion 128/distal face 134, may be configured to generally center the spoon 112 within the concaved surface 14a of the tibia 10 and associated femoral condyle 106a. Once the spoon 114 is positioned, the pin 120 may be advanced along the channel 118 and through the passageway 136 and into the femur 102. As shown, the distal end 121 of the pin 120 may be configured to engage and pierce the bone 102 to create a substantially longitudinal bore within the bone 102 (shown in FIG. 15).

Figure 11:
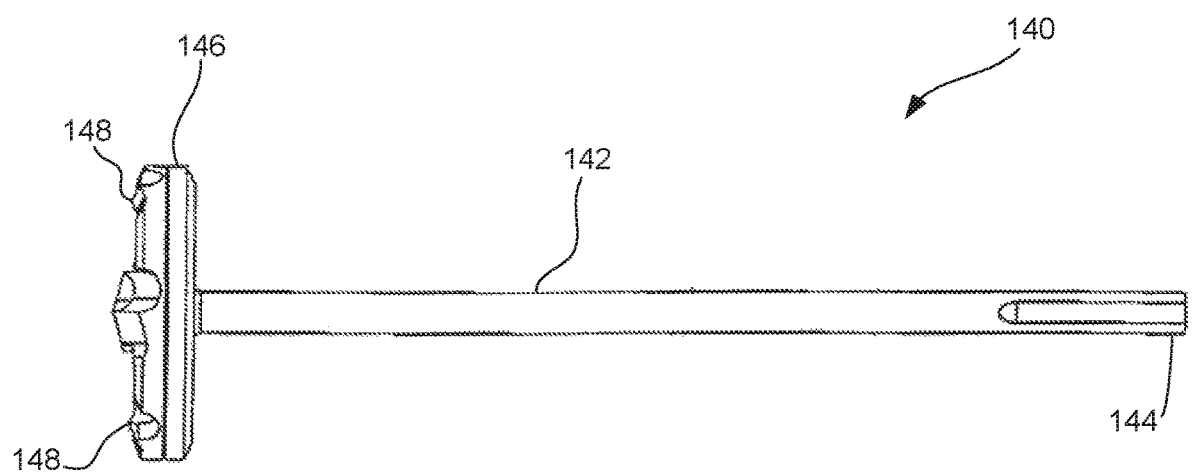
FIGS. 11 and 12 are side and perspective views of one embodiment of a surface reamer consistent with the present disclosure.
Figure 12:
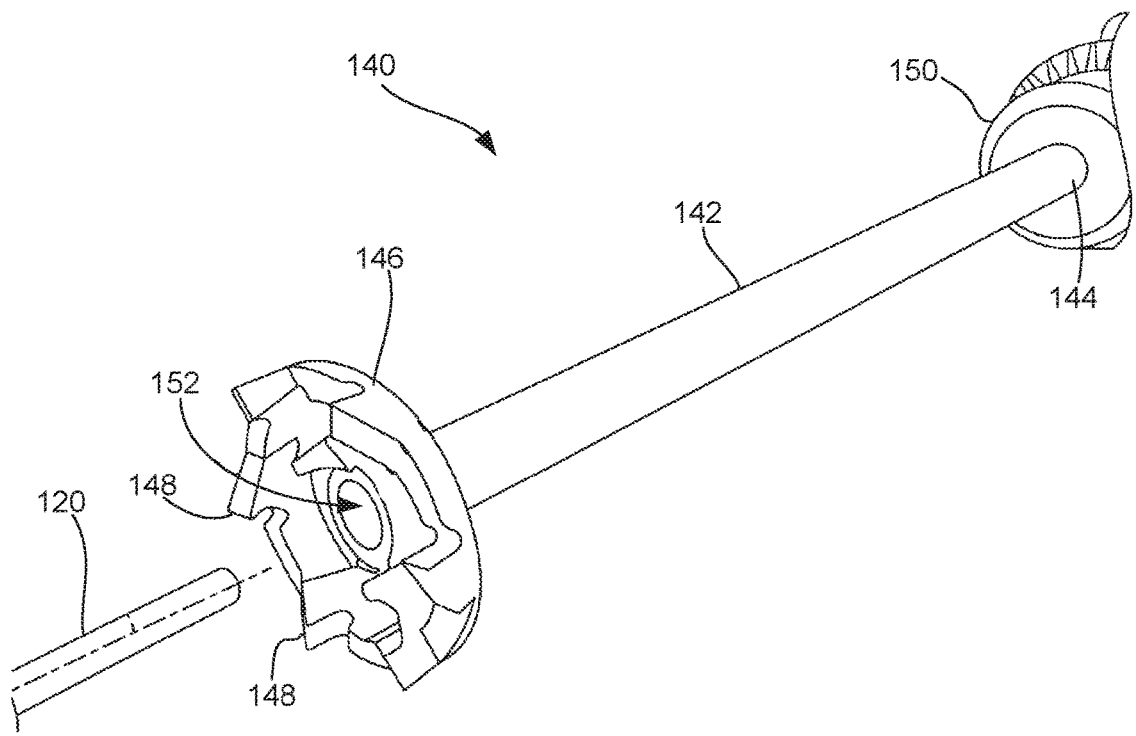

Turning now to FIGS. 11 and 12, side and perspective views of a surface reamer 140 consistent with the present disclosure is generally illustrated. As described in greater detail herein, the surface reamer 140 may be configured to remove a portion of bone and form a first excision site 141 (shown in FIG. 15) on the articular surface 104 of the femoral condyle 106a adjacent the pin 120. As shown, the surface reamer 140 includes a cannulated body 142 having a proximal end 144 and an opposing distal end 146. The distal end 146 includes one or more cutting surfaces 148 configured to remove bone and the proximal end 144 is configured to be coupled to a drill 150 (e.g., a hand drill, electric drill, pneumatic drill or the like).

The drill 150 may be configured to drive (e.g. rotate) the distal end 146 and, in turn, the cutting surfaces 148 of the surface reamer 140 to facilitate bone removal when the cutting surfaces 148 engage bone of the femur 102. As shown, the body 142 of the surface reamer 140 is cannulated (e.g. include a passageway 152 extending the length thereof), allowing the surface reamer 140 to be disposed over the alignment pin 120 along a reference axis A.

Figure 13:
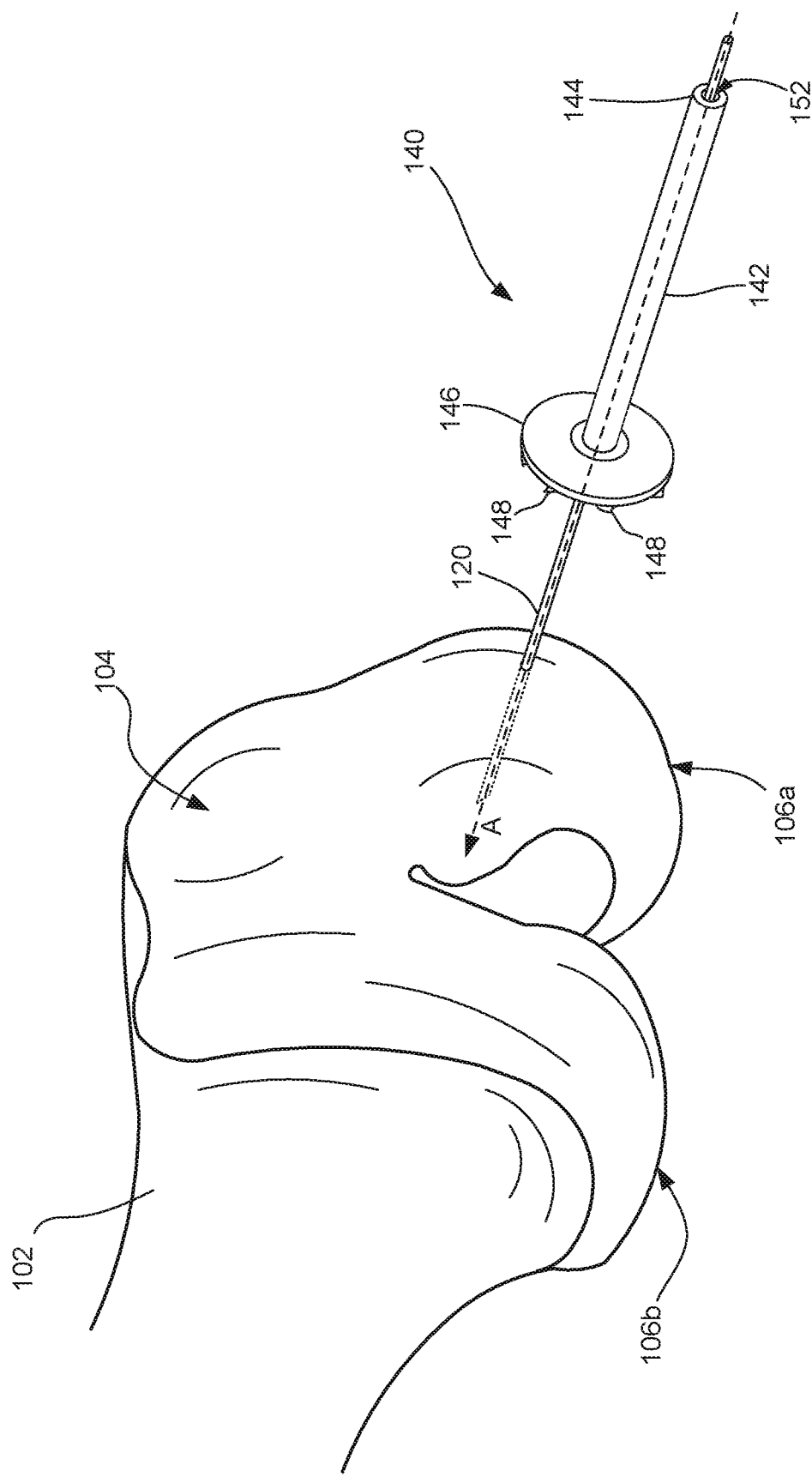
FIGS. 13 and 14 are perspective views of the surface reamer of FIGS. 11 and 12 aligned with the pin and engaging the femur consistent with the present disclosure.
Figure 14:
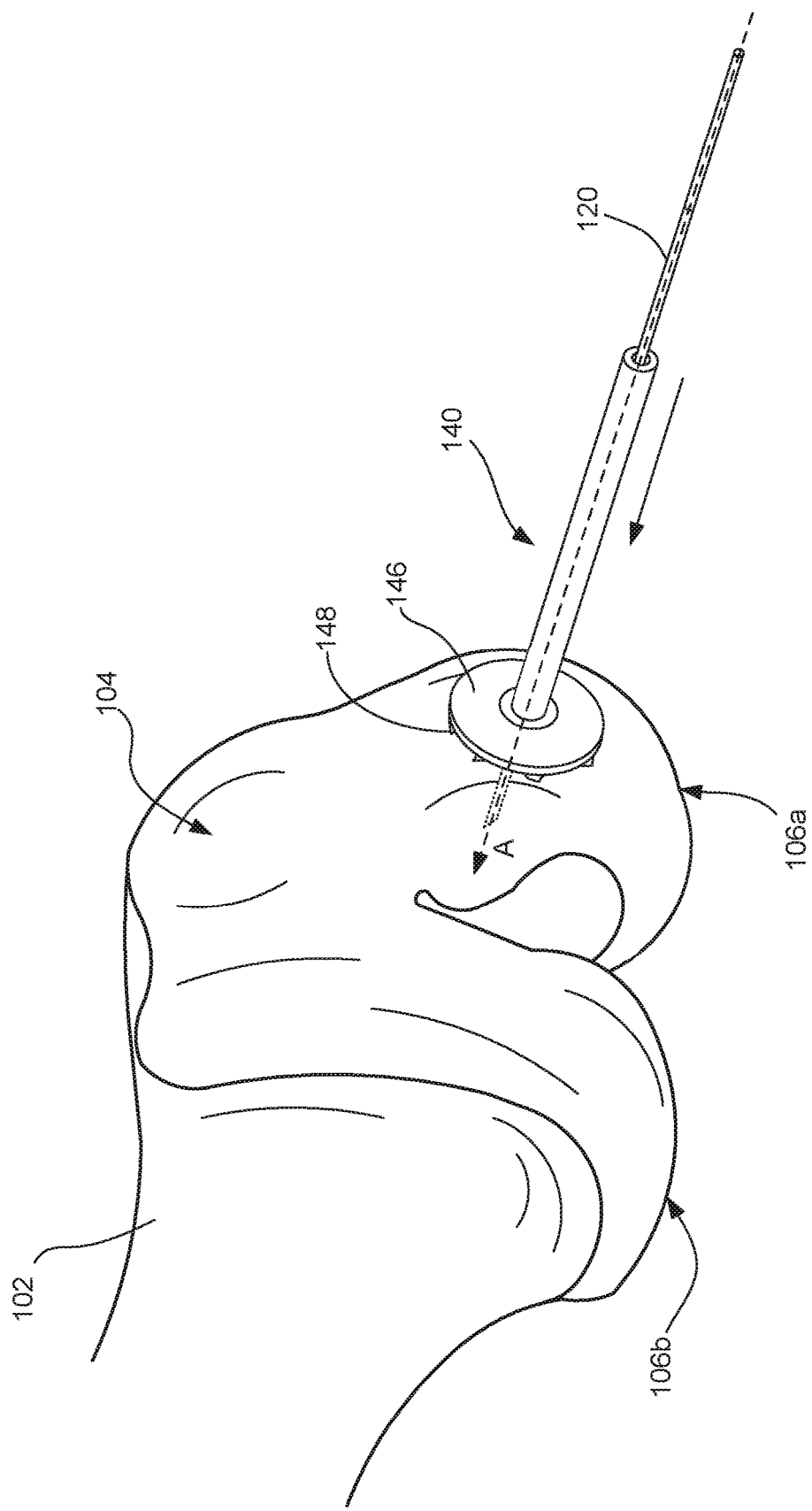

FIGS. 13 and 14 are perspective views of the surface reamer 140 aligned with the pin 120 and engaging a portion of the femoral condyle 106a consistent with the present disclosure. As shown, the surface reamer 140 may be advanced over the pin 120 along a reference axis A. The surface reamer 140 may include an indicia (for example, an opening/window, laser marker, or the like) configured to control the depth of the first excision site to be formed. For example, the indicia may include a laser marking or the like configured to be aligned with the articular surface 104. The indicia may also include an opening/window or the like which may be aligned with an indicia on the pin 120. The cutting surfaces 148 may optionally be positioned about the surface reamer 140 to leave more material proximate the pin 120 along the reference axis A to facilitate removal and insertion of devices further along the method.

The surface reamer 140 may have a specific geometry and/or pattern to minimize vibrations and improve tactile feel while negotiating an interrupted cut on the articular surface 104 of the femoral condyle 106a. The diameter of the surface reamer 140, including the diameter of the proximal end 146, may be selected based on, for example, the desired size of implant to be positioned thereon. Once the first excision site 141 has been formed about the reference axis A, the surface reamer 140 may be removed from the pin 120.

Figure 15:
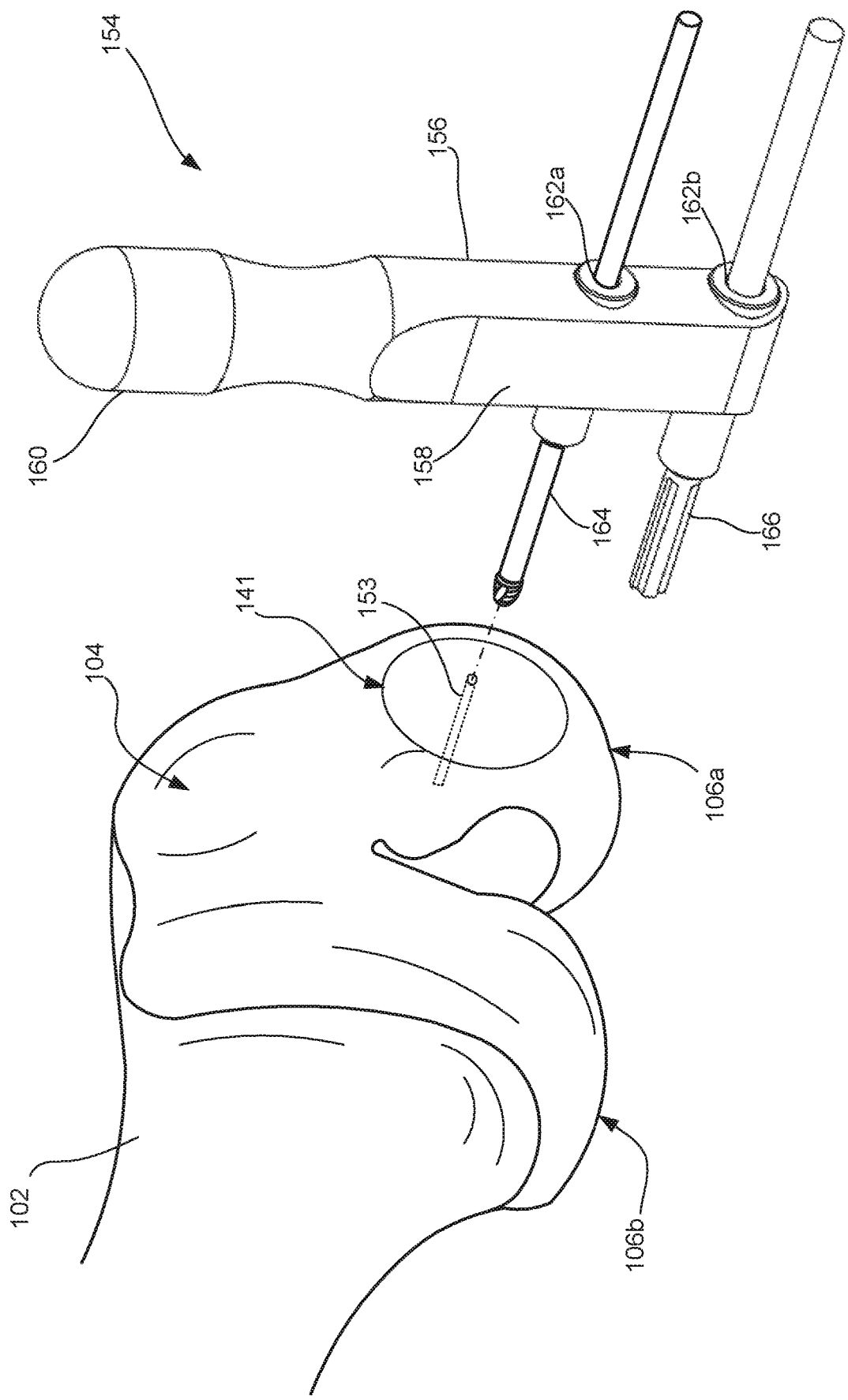
FIG. 15 is a perspective view illustrating one embodiment of a second guide configured to be coupled to the femur consistent with the present disclosure.

Turning now to FIG. 15, a perspective view of one embodiment of a second guide 154 configured to be coupled to the femur 102 is generally illustrated consistent with the present disclosure. As shown, the second guide 154 may include a jig 156 having a body portion 158 including a handle 160 disposed at one end and first and second passageways 162a, 162b defined at an opposing end. The first and second passageways 162a, 162b may each define a generally cylindrical core pathway. The first passageway 162a may be shaped and/or sized to receive and retain a support rod 164 therein. As previously described, advancement of the pin 120 into the bone 102 may form a substantially longitudinal bore 153 within the bone 102 (particularly the femoral condyle 106a having the defect 108 to be repaired). The support rod 164 may be configured to secure the second guide 154 to the femoral condyle 106a. More specifically, a portion of the support rod 164 may be received within a portion of the bore 153 formed in the femoral condyle 106a and may be securely coupled to the bone 102. The second passageway 162b may be shaped and/or sized to receive and retain a drill bit 166 which may be used to form an excision site on the articular surface of the femoral condyle 106a.

As described in greater detail herein, the first and the second passageways 162a, 162b may be offset relative to each other (i.e., the first and the second passageways 162a, 162b may be separated by a distance generally perpendicular to the longitudinal axes of the first and the second passageways 162a, 162b, such that the depth of excision site formed by the drill bit in the articular surface of the femoral condyle 106a may be dictated by such a distance between the first and second passageways 162a, 162b).

Figure 16:
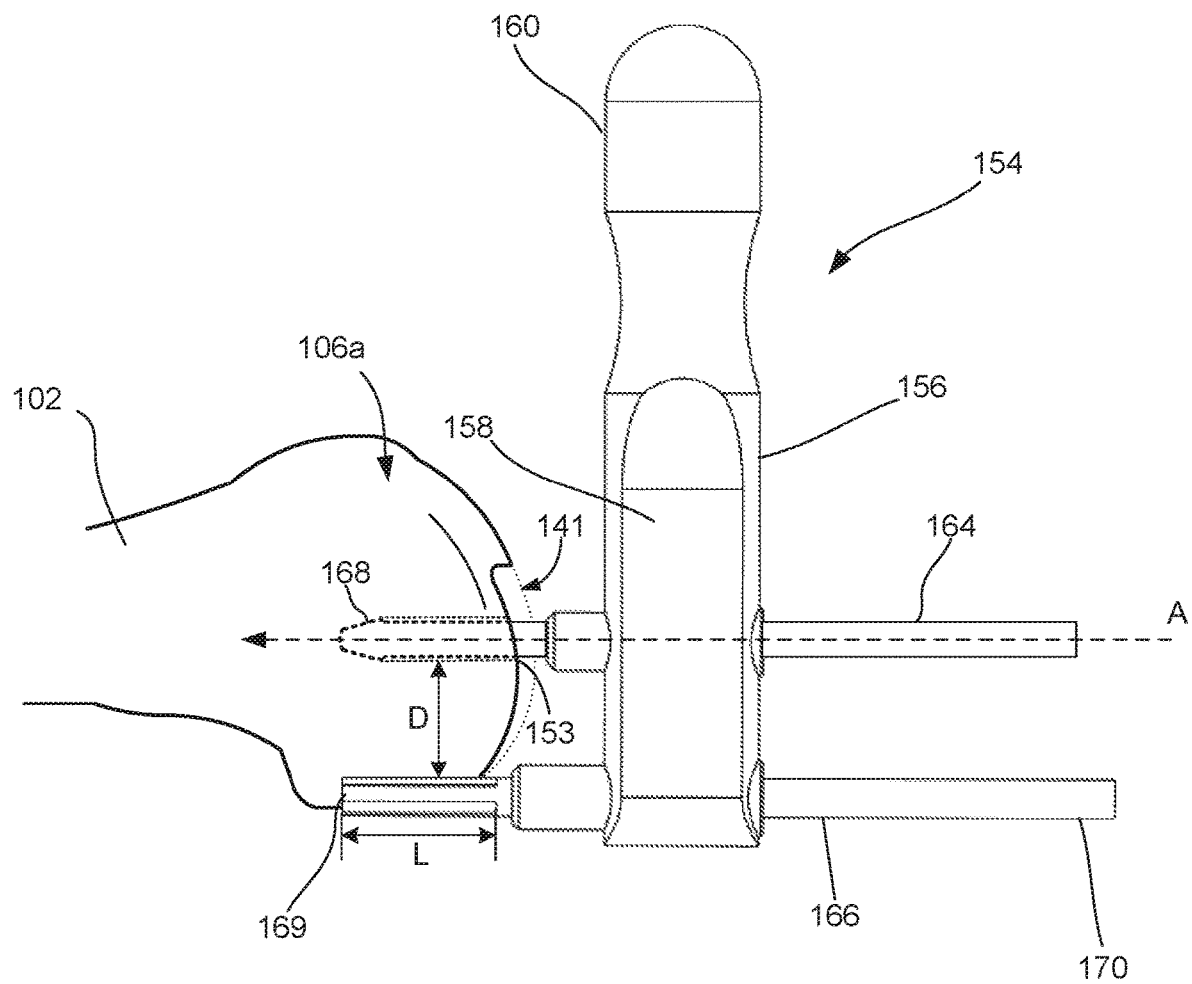
FIG. 16 is a side plan view of one embodiment of a second guide coupled to the femur as generally shown in FIG. 15 consistent with the present disclosure.

As shown in FIG. 16, the second guide 154 may be secured to the femur 102 by the support rod 164. In the illustrated embodiment, the pin 120 may be removed from the femur 102, leaving the bore 153 exposed and the support rod 164 may include a distal end 168 configured to be driven into the bore 153 and securely couple the support rod 164 within the bone 102. In other embodiments, the pin 120 may remain secured within the bore 153 and the support rod 164 may be configured to be disposed over the pin 120 (e g cannulated) and secured within the bone 102.

As shown, the support rod 164 may serve as an axis (generally aligned with reference axis A) about which the jig 156, and ultimately the drill bit 166, may rotate, as described in greater detail herein. Upon advancing the support rod 164 into the bore 153 and thereby securely coupling the second guide 154 to the femoral condyle 106a, a portion of the drill bit 166 may be positioned adjacent a portion of the articular surface of the femoral condyle 106a having the defect 108 to be repaired. More specifically, the drill bit 166 may include a cutting surface 169 positioned adjacent the articular surface and configured to form a second excision site in the articular surface of the femoral condyle 106a and/or bone beneath the articular surface. The drill bit 166 may further include a shank portion 170. The shank portion 170 may include a multi-faceted proximal end configured to be secured to a drill (e.g., a hand drill, electric drill, pneumatic drill or the like). Alternatively, a proximal end of the drill bit 166 may be directly coupled to the drill.

Figure 17:
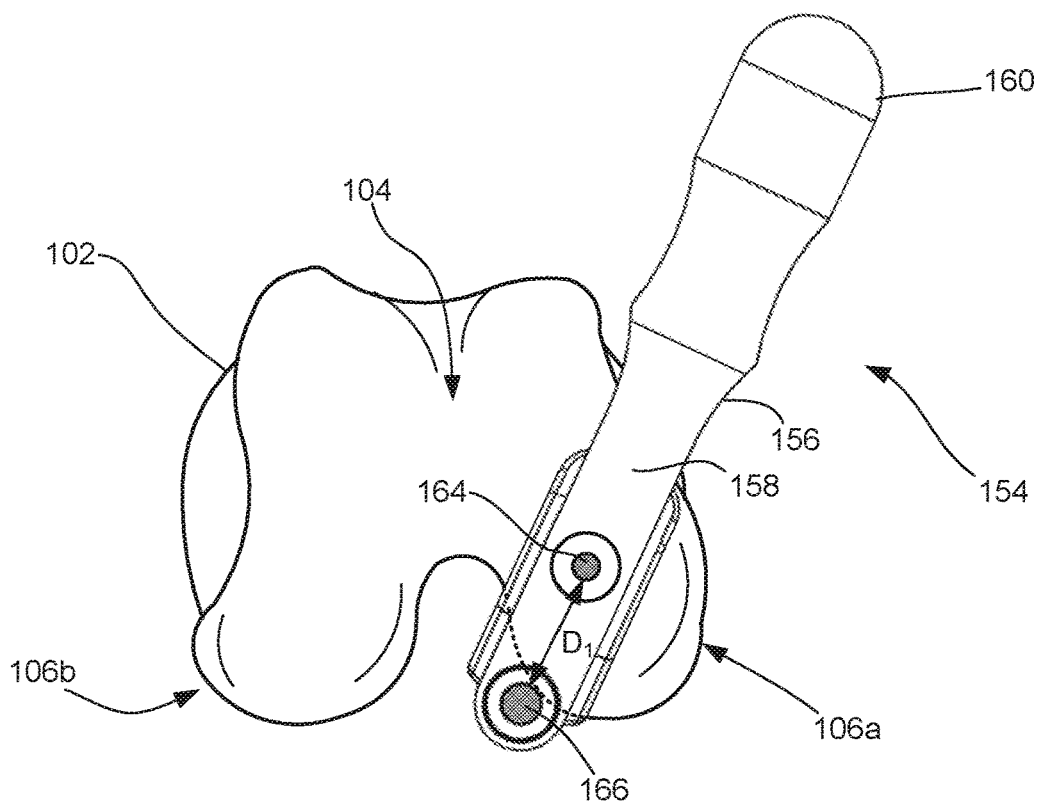
FIG. 17 is a front view of the second guide coupled to the femur in a first position consistent with the present disclosure.
Figure 18:
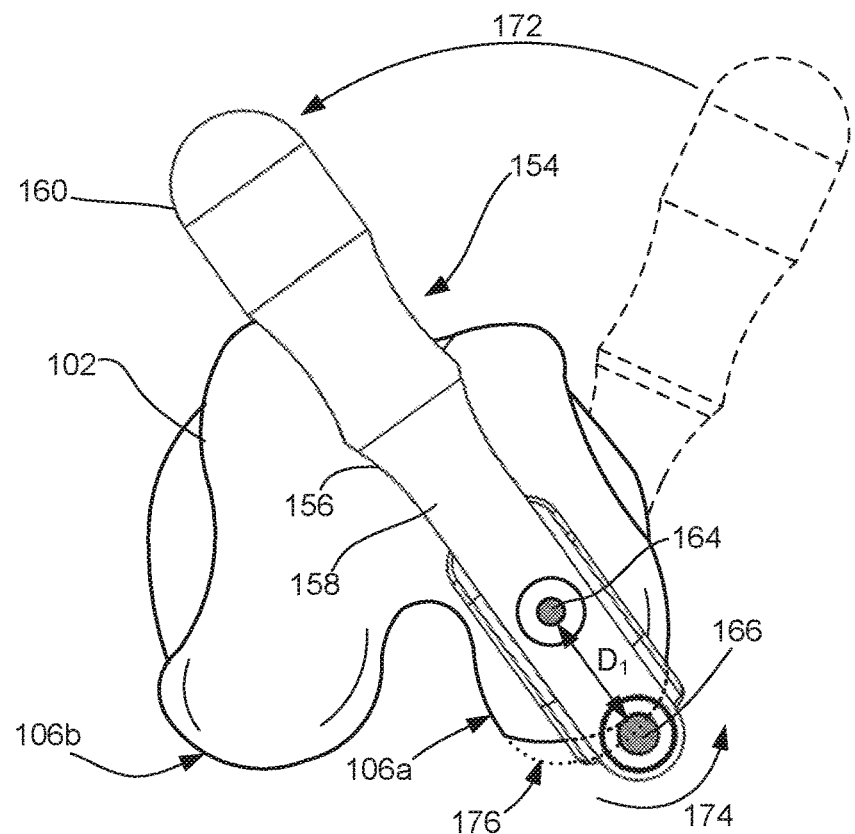
FIG. 18 is a front view of the second guide coupled to the femur and moving from the first position to a second position.

FIGS. 17 and 18 are frontal views of the second guide 154 coupled to the femur 102 by way of the support rod 164. More specifically, FIG. 17 illustrates the second guide 154 in a first position and FIG. 18 illustrates the second guide 154 moving from the first position to a second position and forming a second excision site 176 in the femur 102. As previously described, the support rod 164 may serve as an axis about which the jig 156, including the drill bit 166, may rotate. When the second guide 154 is in the first position, as shown in FIG. 17, the drill bit 166 is adjacent a portion of femoral condyle 106a and may not directly engage the femoral condyle 106a. The second excision site 176 may be formed in the articular surface of the femoral condyle 106a and/or bone beneath by moving the second guide 154 from the first position to the second position, as shown in FIG. 18. More specifically, a user may use the handle 160 of the jig 156 to rotate the jig 156 from the first position to the second position. As the jig 156 is rotated about the support rod 164, as indicated by arrow 172, the drill bit 166 may also rotate about the support rod 164, as indicated by arrow 174, thereby causing the drill bit 166 to advance towards the femoral condyle 106a. As the drill bit 166 advances towards the femoral condyle 106a, a portion of the cutting surface 169 of the drill bit 166 engages the articular surface of the femoral condyle 106a and/or the bone beneath, thereby forming the second excision site 176. As the jig 156 continues to rotate about the support rod 164, the drill bit 166 further advances towards and engages uncut articular surface and/or bone of the femoral condyle 106a to form the second excision site 162. The user may stop rotating the jig 156 once the desired size and/or shape of the second excision site 176 has been formed.

As may be appreciated, the only portion of the femoral condyle 106a, including articular surface and/or bone beneath, that is cut by the drill bit 166 corresponds to the distance D between the support rod 164 and the drill bit 166, and the length L of the cutting surface 169 of the drill bit 166. As generally understood, the distance D may vary depending on the desired depth in the anterior-posterior plane (i.e., from the posterior surface of the femur 102 and extending generally towards the anterior surface of the femur 102). Similarly, the length L may vary depending on the desired depth in the superior-inferior plane (i.e. from the inferior, or lower extremity, portion of the femur 102 and extending generally towards the superior, or upper extremity, portion of the femur 102). As such, the distance D and length L may each be selected to remove the least amount of material so as to control the depth of the second excision site 176 (i.e., the length of the second excision site 176 as measured across the articular surface of the femoral condyle 106a in both the anterior-posterior and superior-inferior planes).

Figure 19:
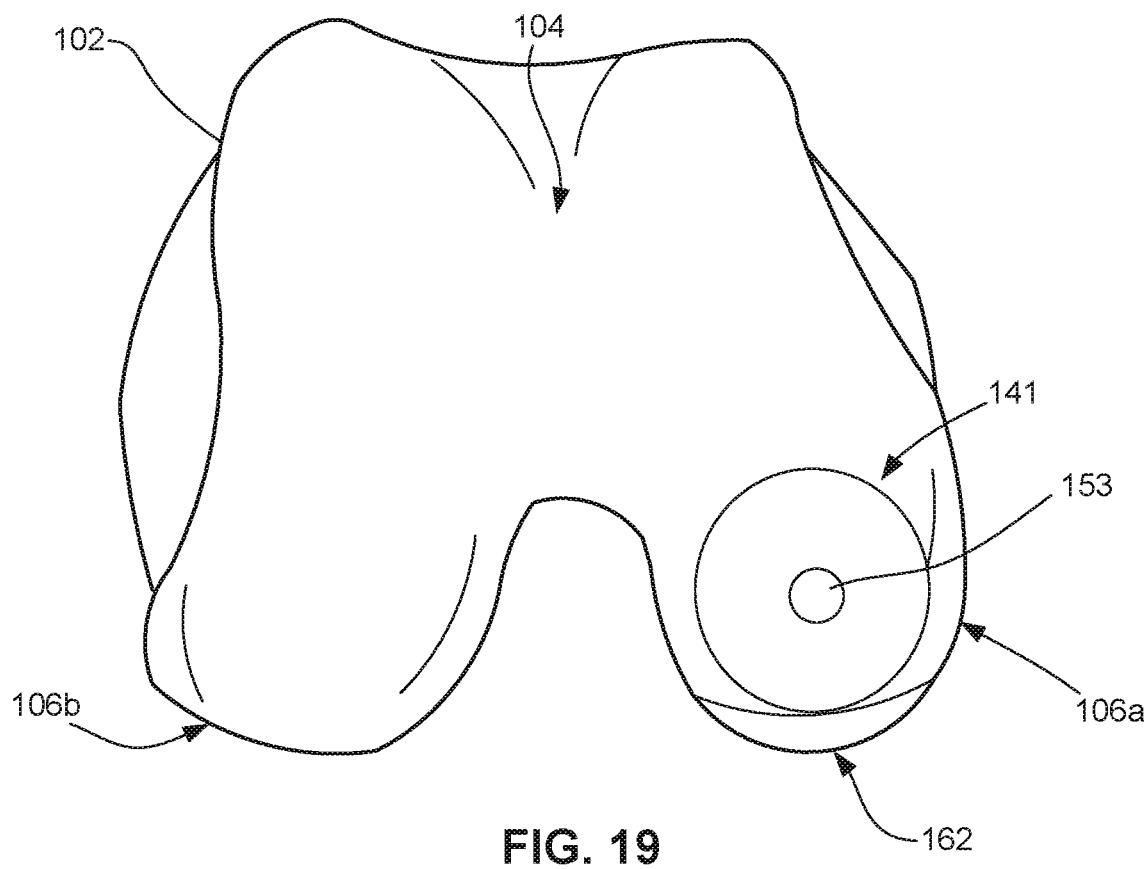
FIGS. 19 and 20 are front and side views of one embodiment of first and second excision sites formed on an articular surface of a femoral condyle using the reamer and second guide consistent with the present disclosure.
Figure 20:
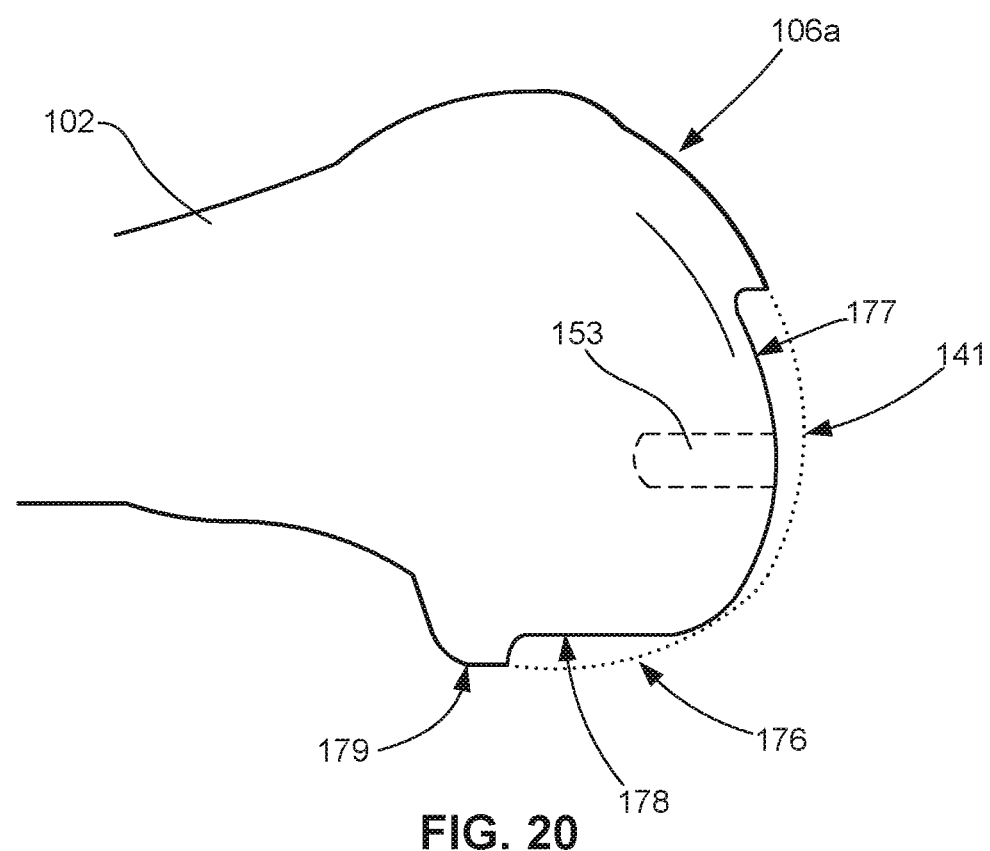

FIGS. 19 and 20 generally illustrate one embodiment of the first and second excision sites 141, 174 corresponding to the surface reamer 140 and drill bit 166, respectively. As shown, the first excision site 141 may extend along a portion of the articular surface of the femoral condyle 106a proximate the longitudinal bore 153 and generally along the superior-inferior and medial-lateral planes. For example, the first excision site 141 may extend from the inferior portion of the femur 102 to the superior portion. The second excision site 176 may extend along the articular surface of the femoral condyle 106a generally along the anterior-posterior and superior-inferior planes. For example, the second excision site 176 may extend from the posterior face of the femoral condyle 106a generally towards the anterior face and from the inferior portion of the femur 102 to the superior portion. The first and second excision sites 141, 176 may collectively serve as an implant site for a femoral condyle implant to be received within, as described in greater detail herein.

As shown, the first excision site 141 includes a base portion 177 configured to receive a portion of the femoral condyle implant. Similarly, the second excision site 176 includes a base portion 178 configured to receive a portion of the femoral condyle implant. The second excision site 176 has been illustrated extending partially across a portion of the femoral condyle 106a (i.e., the second excision site 176 does not extend completely across the articular surface of the femoral condyle 106a, thus leaving a portion 179 of the articular surface and/or bone beneath remaining). This embodiment may be particularly beneficial since it further minimizes the potential for accidentally damaging the nerve bundle. However, the system and method according to the present disclosure may also allow for the second excision site 176 to extend completely across the articular surface.

Figure 21:
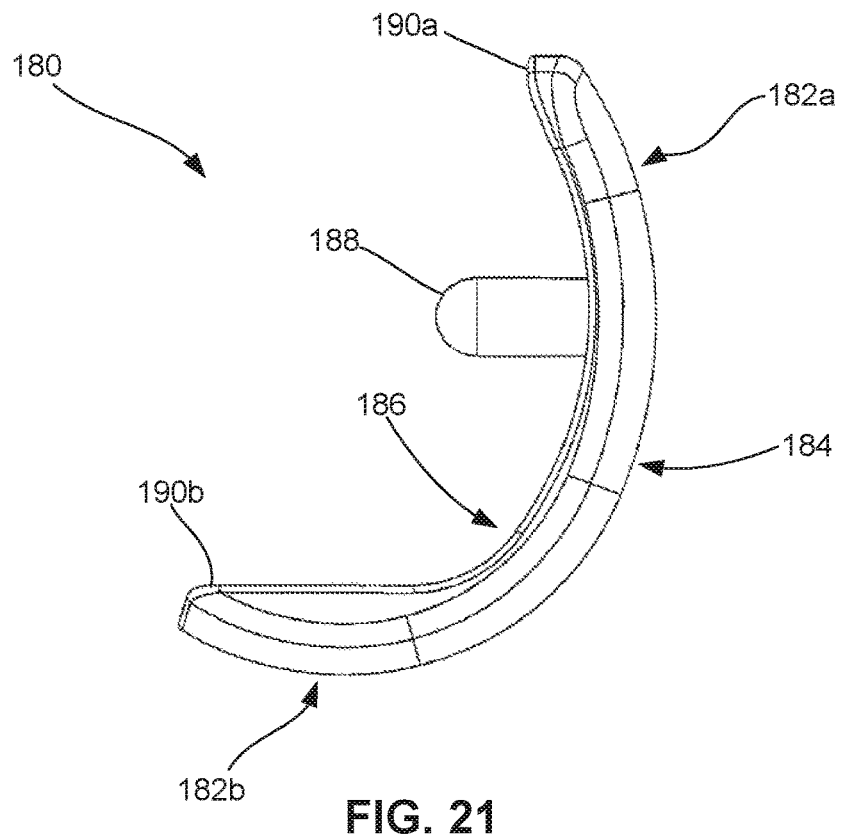
FIGS. 21-23 are side, frontal and perspective views of one embodiment of a femoral implant consistent with the present disclosure.
Figure 22:
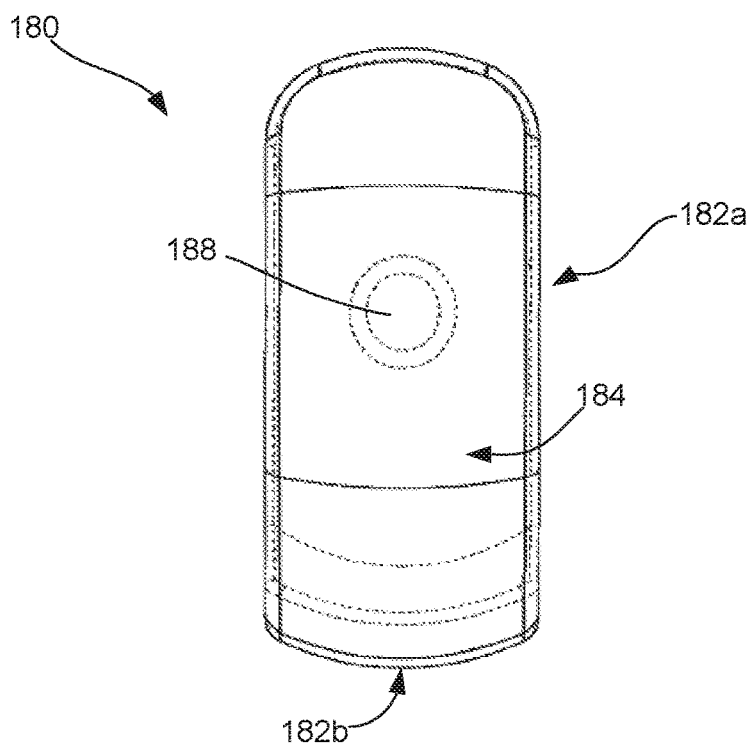
Figure 23:
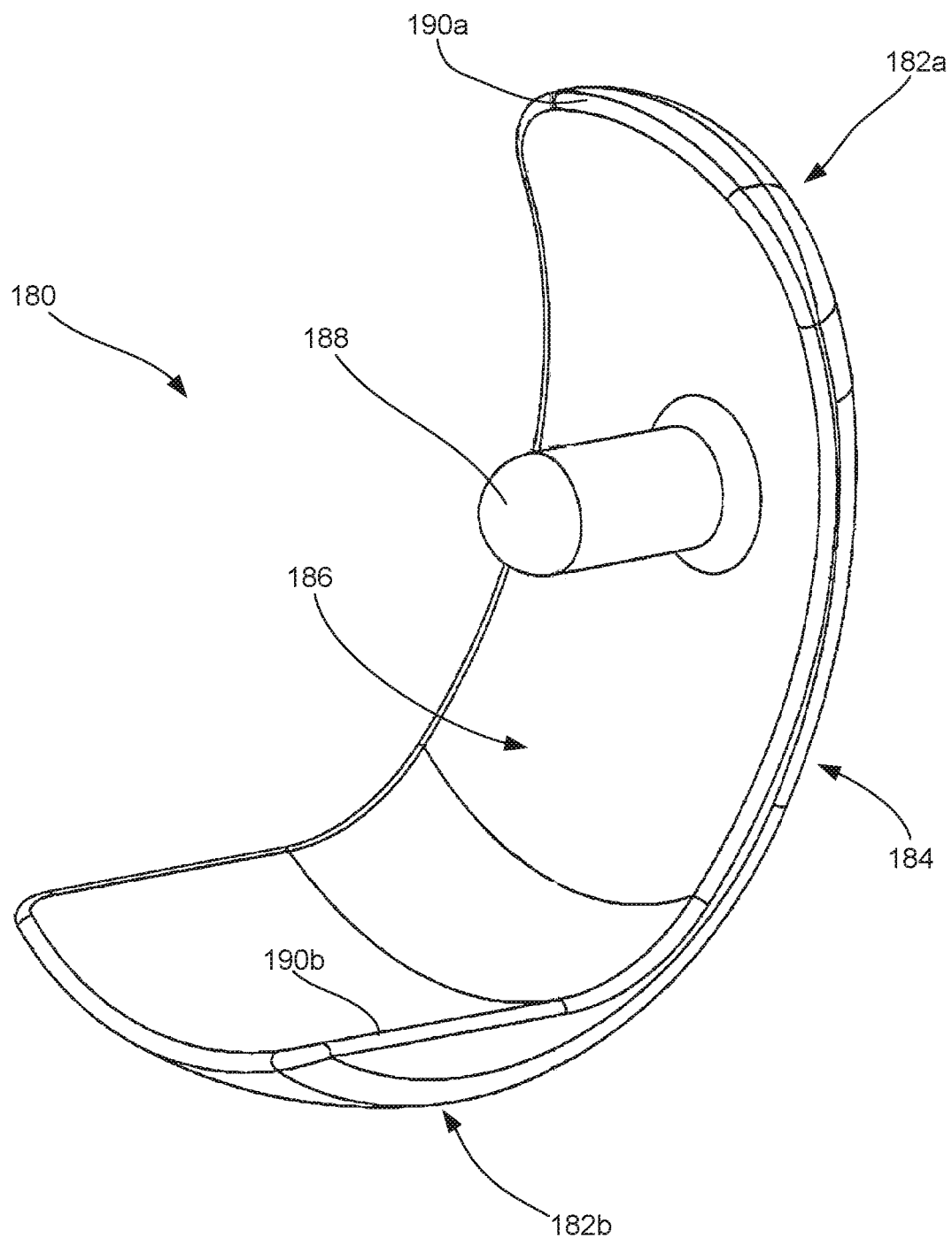

Turning now to FIGS. 21-23, side, frontal and perspective views of one embodiment of a femoral implant 180 consistent with the present disclosure are generally illustrated. In the illustrated embodiment, the femoral implant 180 includes a first portion 182a and a second portion 182b. As generally described in greater detail herein, the first portion 182a may generally correspond to a portion of the femoral condyle 106a proximate the first excision site 141 and the second portion 182b may generally correspond to a portion of the femoral condyle 106a proximate the second excision site 176. As shown, the first and second portions 182a, 182b may be formed from single, unitary structure. It should be noted that in other embodiments, the first and second portions 182a, 182b may be separate components and may be joined to one another by any known means generally understood by one skilled in the art so as to form the femoral implant 180.

The first and second portions 182a, 182b may include a load bearing surface 184 and a bone facing surface 186. The load bearing surface 184 of the first portion 182a may have a surface contour/geometry substantially corresponding to the contour/geometry of the removed femoral articular surface and/or bone of the first excision site 141. Similarly, the load bearing surface 184 of the second portion 182b may have a surface contour/geometry substantially corresponding to the contour/geometry of the removed femoral articular surface and/or bone of the second excision site 176. As such, the load bearing surface 184 may generally correspond to the patient's original articular surface 104 of the femoral condyle 106a, as seen in FIG. 9, for example. The contour/geometry of the load bearing surface 184 may be based on a plurality of measurements taken of the patient's femoral articular surface.

The bone facing surface 186 of the first portion 182a of the femoral implant 180 may have an overall contour/geometry generally corresponding to the contour/geometry of the base portion 177 of the first excision site 141. Similarly, the bone facing surface 186 of the second portion 182b may have an overall contour/geometry generally corresponding to the contour/geometry of the base portion 178 of the second excision site 176. The bone facing surface 186 may include one or more relief cavities, pockets and/or cross-cuts (not shown) configured to enhance securing the implant 180 to the bone 102. The relief cavities may be configured to allow bone regrowth around a portion of the implant 180 and/or promote cement adhesion.

The bone facing surface 186 may optionally include indicia (not shown) representing either inferior and/or superior sides of the implant 180 as well as the size of the implant 180. These indicia may be used by the surgeon to properly align the implant 180 along the inferior-superior and medial-lateral planes within the first and second excision sites.

The bone facing surface 186 may also optionally include one or more rims, ribs or protrusions 190 extending generally away from the bone facing surface 184, for example, as clearly illustrated in FIG. 23. As shown, the rims 190 may extend along the entire periphery of the implant 180. The rims 190 may include a superior rim 190a disposed proximate the first portion 182a of the implant 180 and/or an inferior rim 190b disposed proximate the second portion 182b of the implant 180. The first and second excisions sites 141, 176 corresponding to the rims 190 may be include a contour configured to receive the rims 190.

The implant 180 may further include a fixation member 188 coupled to and extending away from the bone facing surface 186. The fixation member 188 may be configured to be received in the longitudinal bore 153 formed in the articular surface 104 and secure the implant 180 to the femoral condyle 106a. The fixation member 188 may optionally be configured to engage with another fixation element (not shown) configured to be secured into the bore 153 of the patient's bone. For example, the other fixation element may include a post having a threaded outer region configured to engage with an interior surface of the bore 153. The post may include a female opening configured to frictionally engage with the fixation member 188.

Figure 24A:
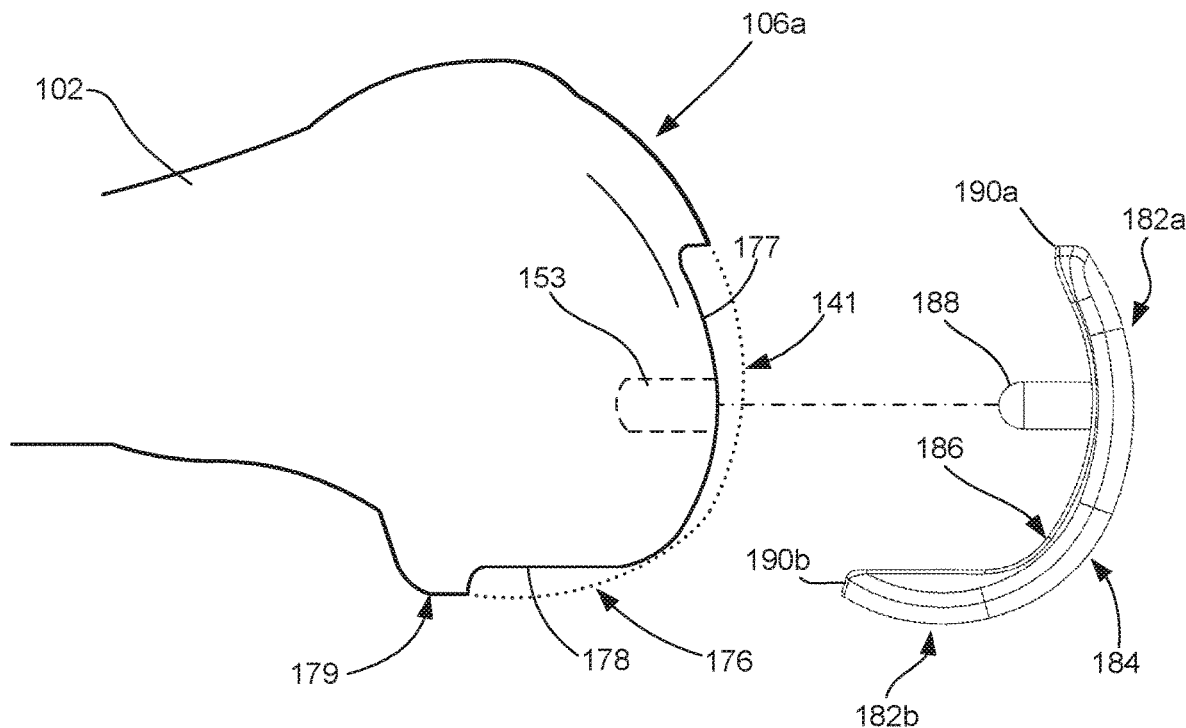
FIGS. 24A and 24B are side views of the femoral implant of FIGS. 21-23 aligned with and coupled to first and second excision sites of the articular surface of the femoral condyle consistent with the present disclosure.
Figure 24B:
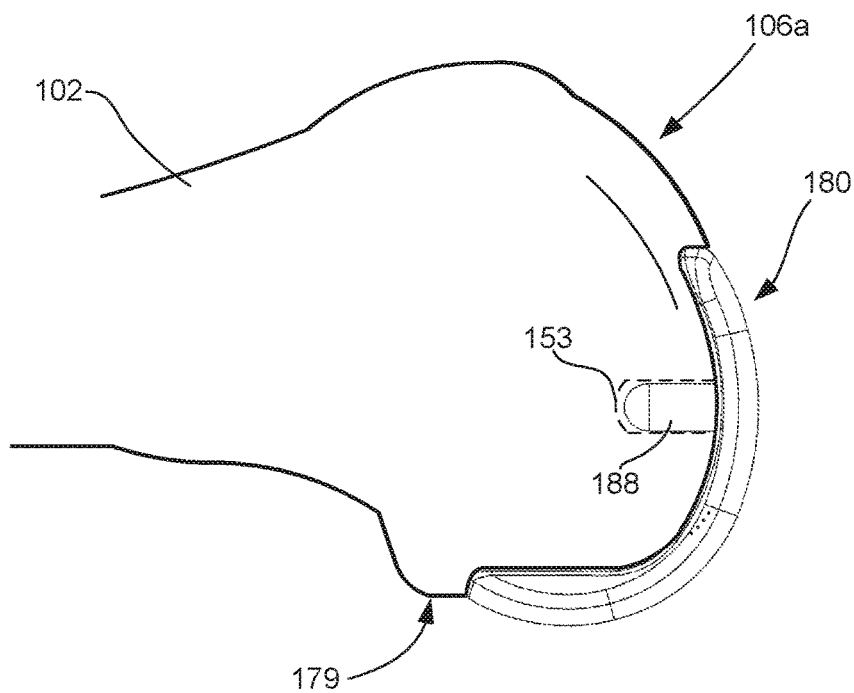

FIG. 24A is a side view of the femoral implant 180 aligned with the femoral condyle 106a (e.g. fixation member 188 is generally aligned with bore 153 along reference axis A). FIG. 24B is a side view of the femoral implant 180 coupled to the first and second excision sites 141, 176 formed in the femoral condyle 106a consistent with the present disclosure. An adhesive (such as, but not limited to, bone cement or the like) may be applied to the bone facing surface 186 and may securely coupled the implant 180 to the bone 102. When coupling the implant 180 to the femoral condyle 106a, the bore 153 may be shaped and/or sized to receive and frictionally engage the fixation member 188 of the implant 180 and the first and second portions 182a, 182b may be received within the first and second excision sites 141, 176.

As may be appreciated from FIGS. 7 and 24B, a femoral implant consistent with at least one embodiment of the present disclosure may be configured to cooperate with a tibial implant consistent with at least one embodiment of the present disclosure. For example, the load bearing surface 184 of the femoral implant 180 may be configured to matingly engage and cooperate with the load bearing surface 72 of the tibial implant 70, thereby allowing flexing of the knee.

According to one aspect, the present disclosure features an implant resection system for preparing an implant site to replace a defect in an articular surface of a first bone. The implant resection system includes a first guide configured to be coupled to a first bone. The first guide includes a body portion having at least one channel defined on a portion thereof. The channel is configured to extend generally perpendicular to a portion of the first bone proximate to the defect. At least one pin is configured to be received and retained within the channel. The pin has a distal end configured to pierce the first bone and to extend and form a longitudinally disposed bore within the first bone.

According to another aspect, the present disclosure features a method for preparing an implant site to replace a defect in an articular surface of a bone. The method includes securing a first guide to a bone. The first guide includes a body portion having at least one channel defined on a portion thereof. The channel is configured to extend generally perpendicular to a portion of the bone proximate to said defect. The method further includes advancing at least one pin along the channel and into the bone and forming a longitudinally disposed bore within the bone. The method further includes removing the pin from the bone and securing a second guide generally perpendicular to the bone proximate to the defect. The second guide includes a body portion having a handle member disposed at one end and a first passageway and a second passageway defined on an opposing end. The passageways each define a generally cylindrical core pathway configured to extend generally perpendicular to the bone. The method further includes forming an excision site on the bone.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

Additional disclosure in the format of claims is set forth below:

What is claimed is:

1. A guide for preparing an implant site to replace a defect in a tibial surface, comprising:
 a jig having a body portion having a first passageway and a second passageway defined therein, wherein the first and second passageways are generally parallel to each other and wherein the first and second passageways each are generally cylindrical;

a first alignment pin and a second alignment pin configured to be advanced through the first passageway and the second passageway, respectively; the first and second alignment pins configured to be advanced into a tibia bone beneath the defect in a tibial surface; wherein the first and second alignment pins each include a depth feature configured to provide a visual indication of the depth of each respective one alignment pin into the tibia bone; and a spoon member coupled to the jig, the spoon member having a generally convex base portion having a contour generally corresponding to a contour of the tibial surface; wherein positioning the spoon member on the tibial surface causes the first and second passageways and the first and second alignment pins to be positioned beneath the defect in the tibial surface.

2. The guide of claim 1, wherein the convex base portion comprises a cross sectional thickness to facilitate advancement of the spoon member between the tibial surface and a femoral condyle.

3. The guide of claim 1, wherein the convex base portion of the spoon substantially matches a contour of a concave portion of the tibial surface.

4. A system for preparing an implant site to replace a defect in a tibial surface, comprising:

a jig having a body portion having a first passageway and a second passageway defined therein, wherein the first and second passageways are generally parallel to each other and wherein the first and second passageways each are generally cylindrical;

at least one alignment pin configured to be advanced through the first passageway or the second passageway; the at least one alignment pin configured to be advanced into a tibia bone beneath the defect in a tibial surface; wherein the at least one alignment pin includes a depth feature configured to provide a visual indication of the depth of the at least one alignment pin into the tibia bone; and a spoon member coupled to the jig, the spoon member having a generally convex base portion having a contour generally corresponding to a contour of the tibial surface; wherein positioning the spoon member on the tibial surface causes the first and second passageways and the at least one alignment pin to be positioned beneath the defect in the tibial surface; and a cannulated drill bit configured to be advanced over the at least one alignment pin to form a first truncated cylindrical excision site in the tibial bone, the cannulated drill bit configured to be advanced over the at least one alignment pin to form a second truncated cylindrical excision site in the tibial bone.

5. The system of claim 4, wherein the convex base portion comprises a cross sectional thickness to facilitate advancement of the spoon member between the tibial surface and a femoral condyle.

6. The system of claim 4, wherein the convex base portion of the spoon substantially matches a contour of a concave portion of the tibial surface.

7. The system of claim 4, wherein the first and second truncated cylindrical excision sites partially overlap one another.

8. The system of claim 4, wherein the cannulated drill bit includes a cutting surface disposed about one end thereof.

9. The system of claim 4, wherein the cannulated drill bit includes a window opening disposed along a length thereof, the window opening configured to enable the depth feature of the at least one alignment pin to be visible through the window when the cannulated drill bit is advanced over the at least one alignment pin.

10. The system of claim 4, wherein the cannulated drill bit includes a shank portion configured to be removably coupled to a drill.

11. The system of claim 4, wherein the depth feature of the at least one alignment pin includes a marking that is alignable with a proximal end of the first and second passageways.

12. The system of claim 4, further comprising a cannulated bushing configured to be advanced over the at least one alignment pin; wherein the cannulated drill bit is configured to be advanced over the cannulated bushing.

13. A system for preparing an implant site to replace a defect in a tibial surface, comprising:

a jig having a body portion having a first passageway and a second passageway defined therein, wherein the first and second passageways are generally parallel to each other and wherein the first and second passageways each are generally cylindrical;

at least one alignment pin to be advanced through the first passageway or the second passageway; the at least one alignment pin to be advanced into a tibia bone beneath the defect in a tibial surface; wherein the at least one alignment pin includes a depth feature configured to provide a visual indication of the depth of the at least one alignment pin into the tibia bone; and a spoon member coupled to the jig, the spoon member having a generally convex base portion having a contour generally corresponding to a contour of the tibial surface; wherein positioning the spoon member on the tibial surface causes the first and second passageways and the at least one alignment pin to be positioned beneath the defect in the tibial surface;

a cannulated drill bit configured to be advanced over the at least one alignment pin to form a first truncated cylindrical excision site in the tibial bone, the cannulated drill bit configured to be advanced over the at least one alignment pin to form a second truncated cylindrical excision site in the tibial bone; and a tibial implant including a load bearing surface having a surface contour substantially corresponding to the tibial surface and a bone facing surface having a contour substantially corresponding to the first and second excision sites in the tibia bone.

14. The system of claim 13, wherein the convex base portion comprises a cross sectional thickness to facilitate advancement of the spoon member between the tibial surface and a femoral condyle.

15. The system of claim 13, wherein the convex base portion of the spoon substantially matches a contour of a concave portion of the tibial surface.

16. The system of claim 13, wherein the first and second truncated cylindrical excision sites partially overlap one another.

17. The system of claim 13, wherein the cannulated drill bit includes a cutting surface disposed about one end thereof.

18. The system of claim 13, wherein the cannulated drill bit includes a window opening disposed along a length thereof, the window opening configured to enable the depth feature of the at least one alignment pin to be visible through the window when the cannulated drill bit is advanced over the at least one alignment pin.

19. The system of claim 13, wherein the depth feature of the at least one alignment pin includes a marking that is alignable with a proximal end of the first and second passageways.

20. The system of claim 13, wherein the bone facing surface also includes a plurality of cavities formed therein.

* * * * *